United States Patent
Jamieson et al.

(12) 
(10) Patent No.: US 11,904,000 B2
(45) Date of Patent: Feb. 20, 2024

(54) COMPOSITIONS AND METHODS TO ENHANCE CUTANEOUS WOUND HEALING

(71) Applicant: BROWN UNIVERSITY, Providence, RI (US)

(72) Inventors: Amanda M. Jamieson, Providence, RI (US); Meredith Crane, Providence, RI (US); Yun Xu, Thousand Oaks, CA (US)

(73) Assignee: BROWN UNIVERSITY, Providence, RI (US)

( * ) Notice: Subject to any disclaimer, the term of this patent is extended or adjusted under 35 U.S.C. 154(b) by 492 days.

(21) Appl. No.: 16/868,388

(22) Filed: May 6, 2020

(65) Prior Publication Data
US 2020/0353046 A1 Nov. 12, 2020

Related U.S. Application Data

(60) Provisional application No. 62/880,452, filed on Jul. 30, 2019, provisional application No. 62/843,896, filed on May 6, 2019.

(51) Int. Cl.
*A61K 38/19* (2006.01)
*A61K 9/00* (2006.01)
*A61K 47/42* (2017.01)

(52) U.S. Cl.
CPC .......... *A61K 38/195* (2013.01); *A61K 9/0014* (2013.01); *A61K 47/42* (2013.01)

(58) Field of Classification Search
CPC .... A61K 9/0014; A61K 38/195; A61K 47/42; A61L 26/0066; A61L 26/0042; A61L 26/0076; A61L 2300/252
See application file for complete search history.

(56) References Cited

U.S. PATENT DOCUMENTS

| | | |
|---|---|---|
| 5,861,478 A | 1/1999 | Jaynes |
| 6,255,282 B1 | 7/2001 | Jaynes |
| 9,169,315 B2 | 10/2015 | Kalle et al. |
| 2007/0020230 A1 | 1/2007 | Kaps et al. |
| 2008/0199426 A1 | 8/2008 | Sukhatme et al. |
| 2008/0317705 A1 | 12/2008 | Kelly |
| 2012/0231479 A1 | 9/2012 | Puskas et al. |
| 2012/0245079 A1 | 9/2012 | Kranz et al. |
| 2014/0072613 A1 | 3/2014 | Lander et al. |
| 2017/0100335 A1 | 4/2017 | Hemmila et al. |
| 2018/0164298 A1 | 6/2018 | Ali et al. |
| 2018/0209931 A1 | 7/2018 | Davis et al. |
| 2018/0296395 A1 | 10/2018 | Kubek |
| 2019/0021998 A1 | 1/2019 | Hemmila et al. |

FOREIGN PATENT DOCUMENTS

| | | |
|---|---|---|
| WO | 2015143386 A1 | 9/2015 |
| WO | 2017037655 A1 | 3/2017 |
| WO | WO-2017037655 A1 * | 3/2017 ......... A61K 38/1816 |

OTHER PUBLICATIONS

Crane MJ et al. Pulmonary influenza A virus infection leads to suppression of the innate immune response to dermal injury. PLoS Pathog 2018 14(8): e1007212, 1-24 (Year: 2018).*
Tavani S Ask the Nurse: Wound Healing & The Flu, https://www.tumblr.com/debraofamerica, Jan. 12, 2018 (Year: 2018).*
Ridiandries A et al. The Role of Chemokines in Wound Healing. Int J Mol Sci. 2018 19(10) 3217 1-20 (Year: 2018).*
Tavares LP et al. The inflammatory response triggered by Influenza virus: a two edged sword. Inflammation Research 2017 66, 283-302 (Year: 2017).*
ScienceDaily (Fighting lung infection trumps wound healing. https://www.sciencedaily.com/releases/2018/08/180823141024.htm, available Aug. 23, 2018) (Year: 2018).*
Alexeev V et al. Pro-Inflammatory Chemokines and Cytokines Dominate the Blister Fluid Molecular Signature in Patients with Epidermolysis Bullosa and Affect Leukocyte and Stem Cell Migration (Journal of Investigative Dermatology 2017 137(11) 2298-2308 (Year: 2017).*
Crane et al., "Pulmonary Influenza a Virus Infection Leads to Suppression of the Innate Immune Response to Dermal Injury", PLoS Pathog, vol. 14, No. 8, Aug. 23, 2018, pp. 1-24.
Crane et al., "Surviving Deadly Lung infections: innate Host Tolerance Mechanisms in the Pulmonary System", Frontiers in Immunology, vol. 9, Article 1421, Jun. 2018, pp. 1-18.
Lee et al., "Coinfection With Influenza A Virus and Klebsiella oxytoca: An Underrecognized Impact on Host Resistance and Tolerance to Pulmonary Infections", Frontiers in Immunology, vol. 9, Article 2377, Oct. 2018, pp. 1-16.
Lee et al., "Hemorrhage Attenuates Neutrophil Recruitment in Response to Secondary Respiratory Infection by Pseudomonas Aeruginosa", Shock, vol. 52, No. 5, 2019, pp. 506-512.
Lohmann et al., "Glycosaminoglycan-Based Hydrogels Capture Inflammatory Chemokines and Rescue Defective Wound Healing in Mice", Science Translational Medicine, vol. 9, Issue 386, Available online at: https://www.ncbi.nlm.nih.gov/pubmed/28424334, Apr. 19, 2017, pp. 1-13.
Ridiandries et al., "Broad Spectrum Inhibition of the CC-Chemokine Class Improves Wound Healing and Wound Angiogenesis", International Journal of Molecular Science, vol. 18, No. 1, Article 155, Available online at: https://www.ncbi.nlm.nih.gov/pubmed/28098795, Jan. 2017, pp. 1-15.

* cited by examiner

*Primary Examiner* — Karen A. Canella
*Assistant Examiner* — John J Skoko, III
(74) *Attorney, Agent, or Firm* — Adler Pollock & Sheehan P.C.; Michel Morency

(57) ABSTRACT

The present invention provides compositions and methods to enhance cutaneous wound healing in subjects afflicted with, or at risk for, a pulmonary infection and/or a pulmonary injury. More specifically, the embodiments of the present invention relate to using fibrin carrier as a vehicle to topically deliver one or more chemokine onto a cutaneous wound so as to accelerate wound healing.

12 Claims, 12 Drawing Sheets

COMPOSITIONS AND METHODS TO ENHANCE CUTANEOUS WOUND HEALING

CROSS REFERENCE TO RELATED APPLICATIONS

This application claims priority to U.S. Provisional Application Ser. No. 62/843,896, filed on May 6, 2019, and priority to U.S. Provisional Ser. No. 62/880,452, filed on Jul. 30, 2019. The entirety of Provisional Application 62/843,896 and the entirety of Provisional Application 62/880,452 are incorporated by reference herein.

STATEMENT REGARDING FEDERALLY SPONSORED RESEARCH OR DEVELOPMENT

This invention was made with government support under grant numbers R01 HL126887 and P20 GM109035 awarded by the National Institutes of Health and grant number D15AP00100 awarded by the Defense Advanced Research Projects Agency. The government has certain rights in the invention.

FIELD OF THE INVENTION

The embodiments of the present invention relate to compositions and methods to enhance cutaneous wound healing in subjects at risk for or afflicted with a pulmonary infection and/or a pulmonary injury.

BACKGROUND OF THE INVENTION

Studies of immune system function have classically been focused on single-insult encounters, such as infection or injury. Much less is known about how multi-insult encounters are managed by the innate immune system. Pneumonia is a risk of hospitalization, especially in post-surgery and trauma.[23,24,26,28,35] Although post-surgical pneumonia is a well-known clinical complication, very little is known about the interaction between pulmonary infection and inflammation in other tissues (e.g., dermal tissues), which occurs in the clinical setting as post-traumatic pneumonia.

The mobilization of innate leukocytes, including monocytes and neutrophils, to sites of injury is a critical initial step in wound repair, and disruption of this process can affect the body's ability to recover. Co-occurring inflammatory sites, as seen in cases of post-traumatic pneumonia, may alter the directed migration of leukocytes. Patients in the hospital with traumatic injuries rely on an intact innate immune response to drive acute wound healing. [19,22-25] However, the innate immune response is also essential in preventing and clearing infections, raising the possibility that there will be increased stress on the immune response during the post-wounding recovery period if complicated by a concurrent infection.[1-16] Indeed, surgery or trauma can affect the pulmonary immune response, leaving patients susceptible to a variety of complications, including wound infection or systemic secondary infections[26] permanent disablement, and increased mortality.[29,30] Furthermore, the treatment of poorly healing wounds presents a major economic burden to society and the healthcare system.[31,32] However, the impacts of pulmonary infection or pulmonary injury on the ability to heal a wound at a distal site, and how the cellular innate immune response prioritizes these inflammatory sites, has not been well described.

Accordingly, there is a need for a better understanding of inflammatory events co-occurring in the body, and how the innate immune response is directed in this setting.

BRIEF SUMMARY OF THE INVENTION

The present invention is related to compositions and methods to enhance cutaneous wound healing in subjects at risk for or afflicted with a pulmonary infection and/or a pulmonary injury. Post-surgical pneumonia is a well-known clinical complication that exemplifies the need for two distinct innate immune response. Lung infections are thought to directly increase morbidity and mortality in these patients. However, using data from a cohort of midline abdominal incision patients, we have uncovered an additional and critical complication of pneumonia in surgical patients: decreased wound healing. Slower healing predisposes those patients to further complications including infection, scarring, disability, and increased mortality. Patients with poor healing wound have high medical care costs. The data presented herein shows that there is a decrease in several chemokines that are important to attracting innate immune cells that are essential to healing wounds.

To increase wound healing in at-risk patients, the present invention provides compositions and methods using fibrin spray as a vehicle to topically deliver recombinant protein to manipulate chemokines to improve wound healing responses. The application of a fibrin carrier, such as a fibrin spray or sealant, with recombinant proteins, such as CXCL1 and CCL2, onto a cutaneous wound leads to accelerated wound healing. It has the advantages of the ease of application, the strong efficacy as well as the usage of already approved clinical products.

The present invention provides a method of enhancing cutaneous wound healing in subjects at risk for or afflicted with a pulmonary infection and/or a pulmonary injury comprising administering to the wound a composition comprising (a) one or more chemokine and (b) a fibrin carrier. In one embodiment, the one or more chemokine is one or more inflammatory chemokine. In another embodiment, the one or more inflammatory chemokine is a combination of one or more monocyte chemoattractant and one or more neutrophil chemoattractant. The one or more monocyte chemoattractant is selected from: CXCL4, CXCL10, CXCL17, CX3CL1, CCL1, CCL2, CCL3, CCL4, CCL5, CCL6, CCL7, CCL8, CCL12, CCL13, CCL14, CCL15, CCL16, CCL22, and CCL23. The one or more neutrophil chemoattractant is selected from: CXCL1, CXCL2, CXCL3, CXCL4, CXCL5, CXCL6, CXCL7, CXCL8, CXCL15, CCL9, CCL10, CCL20, CCL23, and CCL24. In one embodiment, the monocyte chemoattractant is CCL2 and the neutrophil chemoattractant is CXCL1.

In another aspect, the present invention provides a method of enhancing cutaneous wound healing in subjects at risk for or afflicted with a pulmonary infection and/or a pulmonary injury comprising administering to the wound a composition comprising (a) one or more monocyte chemoattractant; (b) one or more neutrophil chemoattractant; and (c) a fibrin carrier. The one or more monocyte chemoattractant is selected from: CXCL4, CXCL10, CXCL17, CX3CL1, CCL1, CCL2, CCL3, CCL4, CCL5, CCL6, CCL7, CCL8, CCL12, CCL13, CCL14, CCL15, CCL16, CCL22, and CCL23. The one or more neutrophil chemoattractant is selected from: CXCL1, CXCL2, CXCL3, CXCL4, CXCL5, CXCL6, CXCL7, CXCL8, CXCL15, CCL9, CCL10, CCL20, CCL23, and CCL24. In one embodiment, the monocyte chemoattractant is CCL2 and the neutrophil chemoattractant is CXCL1.

In another aspect, the present invention provides a method of enhancing cutaneous wound healing in subjects at risk for or afflicted with a pulmonary infection and/or a pulmonary injury comprising administering to the wound a composition comprising (a) CCL2; (b) CXCL1; and (c) a fibrin carrier.

Other implementations are also described and recited herein.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings:

In FIG. 5k, #denotes a statistically significant change between K. oxytoca and rCCL2/rCXCL2+K. oxytoca. In FIG. 5a-j, % indicates a statistically significant change between wound+PBS and wound+rCCL2/rCXCL2+K. oxytoca, and #indicates a statistically significant change between wound+PBS+K. oxytoca and wound+rCCL2/rCXCL2+K. oxytoca.

FIG. 6b shows that pulmonary K. oxytoca infection causes reduced wound cellularity at early wound time points. Pulmonary infection was performed on wounding day 1, and wound cell number was recorded on wounding days 1, 2, and 3. Data are shown as the mean ±SEM with n=12 mice per group from three independent experiment. % indicates a statistically significant change between wound and wound+K. oxytoca.

DETAILED DESCRIPTION OF THE INVENTION

Figure 1:
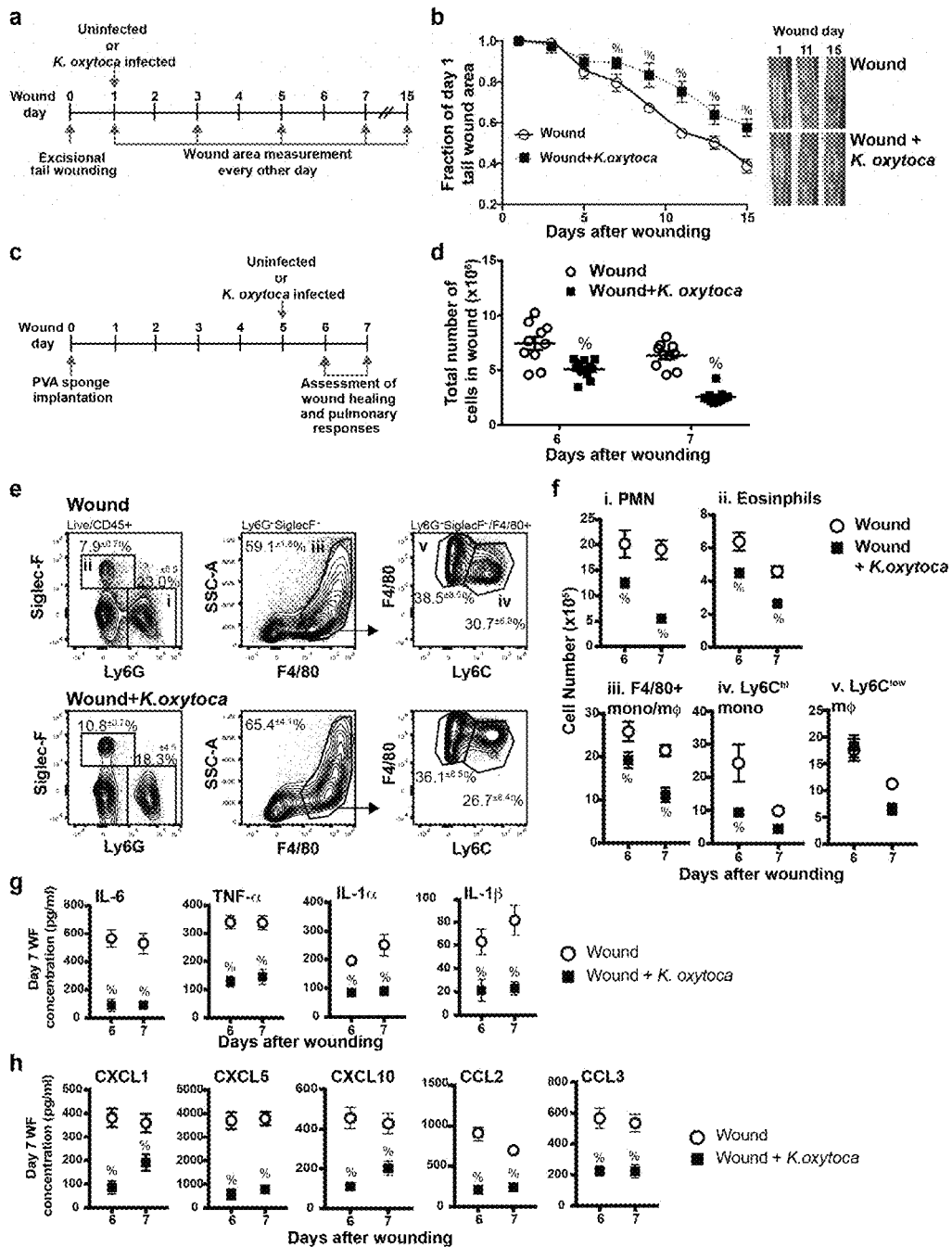
FIG. 1 shows that pulmonary *K. oxytoca* infection impairs the wound healing cellular and cytokine responses. To determine the effect of lung infection on wound closure, excisional tail wounds were performed on C57BL/6J mice, which were then uninfected or infected intranasally with *K. oxytoca* on wound day 1. The experiment schematic is shown in FIG. 1a. Tail wound closure was delayed in mice with *K. oxytoca* infection compared to uninfected mice (FIG. 1b). The PVA sponge wound model was used to assess the effects of pulmonary infection on cellular wound healing responses. Sponges were implanted on wound day 0, and mice were uninfected or infected intranasally with *K. oxytoca* on wound day 5. A schematic is shown in FIG. 1c. Wound cellular content was decreased on wound day 6 and day 7 in infected mice compared to uninfected mice (FIG. 1d). Flow cytometry analysis of day 7 wounds shows the frequency of Ly6G$^+$ neutrophils (i), Siglec-F$^+$ eosinophils (ii), F4/80$^+$ monocytes/macrophages (iii), F4/80$^+$Ly6C$^{hi}$ monocytes (iv), and F4/80$^+$Ly6C$^{low}$ macrophages (v) on wound day 7 (FIG. 1e). The absolute number of innate leukocyte populations in day 6 and day 7 wounds is shown in FIG. 1f. A panel of proinflammatory cytokines and chemokines were assayed in day 7 wound fluids using a flow cytometry-based multiplex bead array or ELISA including cytokines TNF-α, IL-6, and IL-1α (FIG. 1g) and chemokines CCL2, CCL3, CXCL10, CXCL1, and CXCL5 (FIG. 1h). Data are shown as the mean ±SEM with minimum n=10 mice per group from three independent experiments. Results are considered statistically significant when p≤0.05. Statistically significant changes between wound and wound+*K. oxytoca* are denoted by %.

It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "subject" refers to a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), but are not so limited. Subjects include human subjects. The human subject may be a pediatric, adult, or a geriatric subject. The human subject may be of either sex.

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

As used herein, the terms "effective amount" and "therapeutically-effective amount" include an amount sufficient to prevent or ameliorate a manifestation of disease or medical condition, such as wound healing. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treating" or "treatment" or "to treat" or "alleviating" or "to alleviate" refer to both (1) therapeutic measures that cure, slow down, lessen symptoms of, and/or halt progression of a diagnosed disease or infection and (2) prophylactic or preventative measures that prevent or slow the development of a disease or infection.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased" "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-micro emulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

For use in the methods of this invention, active compounds can be given per se or as a pharmaceutical composition containing, for example, 0.1 to 99.5% (more preferably, 0.5 to 90%) of active ingredient in combination with a pharmaceutically-acceptable carrier.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art.[56]

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In other embodiments, the active compound will be administered once daily.

The patient receiving this treatment is any animal in need, including primates, in particular humans; and other mammals such as equines bovine, porcine, sheep, feline, and canine; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, l-ascorbic acid, l-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, I-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, I-pyroglutamic acid, salicylic acid, sebacic acid, stearic acid, succinic acid, sulfuric acid, I-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4$^{th}$ ed., Cold Spring Harbor Laboratory Press, Cold Spring Harbor, N.Y., USA (2012) (ISBN 1936113414); Davis et al, Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

Rationale

Studies of single inflammatory insults form the foundation of our understanding of innate immune function. In many instances, inflammatory events co-occur in the body, and how the innate immune response is directed in this setting is not well understood. We hypothesized that the innate immune response prioritizes, or "triages," contemporaneous inflammatory sites. We examined the interaction between dermal inflammation and pulmonary infection, which occurs in the clinical setting as post-traumatic pneumonia. Through a retrospective analysis of surgical patients with abdominal incisions, we determined that decreased surgical wound healing is a complication of post-traumatic pneumonia. We developed murine models that recapitulate this wound-healing defect in vivo, which enabled us to examine the cellular basis of this impairment. We found that pulmonary infection suppressed the trafficking of innate leukocytes, including monocytes and neutrophils, to subcutaneous wounds. Given the importance of innate immunity for both clearing infections and healing wounds, we propose that the inflammatory sites in our model are prioritized, or "triaged," by the immune response. Experimentally, we rescued leukocyte trafficking to the wound and accelerated healing rates in mice with pneumonia by the addition of exogenous chemokines to wounds. These studies suggest that competing chemokine signals from inflamed tissue may direct the prioritization of innate immune cellular responses, and further identify a potential for chemokine-directed therapies to counteract the negative effects of "immune triage" in patients fighting multiple inflammatory insults.

Innovation

The mobilization of innate leukocytes, including monocytes and neutrophils, to sites of injury is a critical initial step in wound repair, and disruption of this process can affect the body's ability to recover. Co-occurring inflammatory sites, as seen in cases of post-traumatic pneumonia, may alter the directed migration of leukocytes. Patients in the hospital with traumatic injuries rely on an intact innate immune response to drive acute wound healing.[1-16] However, the innate immune response is also essential in preventing and clearing infections, raising the possibility that there will be increased stress on the immune response during the post-wounding recovery period if complicated by a concurrent infection.[1-16] Indeed, surgery or trauma can affect the pulmonary immune response, putting patients at an increased risk of developing secondary lung infection, typically from bacterial species including *Staphylococcus aureus, Streptococcus pneunoniae*, and *Klebsiella* spp, although pneumonia of viral, fungal, or acid aspiration etiology can also occur, which results in increased morbidity and mortality.[17-25] However, how pulmonary infection impacts the ability to heal a wound at a distal site, and how the cellular innate immune response prioritizes these inflammatory sites, has not been well described. These questions are addressed herein.

Through a retrospective analysis of clinical data, we describe herein a previously unrecognized increased risk of poor wound healing in surgical patients who develop pneumonia. This observation is significant because delayed wound healing leaves patients susceptible to a variety of complications, including wound infection or systemic secondary infections,[28,29] hernias, debilitating scar tissue formation[30] permanent disablement, and increased morbidity and mortality.[31,32] Furthermore, the treatment of poorly healing wounds presents a major economic burden to society and the healthcare system.[33,34]

Building upon previous work, which demonstrated that pulmonary infection with influenza A virus in mice suppresses wound healing in the skin,[26] the work described herein identifies the cellular basis of impaired wound healing in mice with bacterial pulmonary infection. It has been shown in other systems that disruption of innate immune cellular responses can alter or delay wound healing[1,4,5,7,8,10,27] Because the innate immune response is essential in clearing infections and healing wounds, we proposed that, when faced with both insults, the immune response is skewed toward the lung, thus compromising the quality and magnitude of the wound healing response.

To address these questions at a mechanistic level, we developed mouse models of post-injury pulmonary infection. Complementary dermal wound models were specifically chosen to allow for the assessment of innate immune responses during acute wound healing, as well as the rate of repair. The study described herein shows that, as in human patients, mice with dermal wounds and bacterial pneumonia had decreased wound healing, while maintaining pulmonary innate immune responses and bacterial resistance. Furthermore, this study demonstrates that innate immune leukocyte trafficking defects are responsible for the suppressed wound healing. The wounds in mice with lung infections had reduced cellularity and suppressed inflammatory cytokine and chemokine levels compared to uninfected mice. Adoptive transfer experiments revealed that defects in monocyte and neutrophil trafficking to the wound contributed to the reduction in wound cellularity, likely through the loss of chemotactic signals. Importantly, the loss of leukocyte migration to the wounds of infected mice could be reversed by the addition of chemokines, such as CCL2 and CXCL1, to the wound bed.

These data presented herein support the concept of "innate immune triage," in that the immune system prioritizes its response when faced with multiple inflammatory insults through chemokine-directed cell trafficking. With the immune response directed towards the lungs, poorly healing wounds in patients with hospital-acquired pneumonia may contribute to their increased morbidity. By manipulating this innate immune prioritization in vulnerable populations, wound healing can be improved. The present invention introduces the potential of using chemokine-based treatments to manipulate the prioritization of innate leukocyte responses to improve wound healing in high-risk patient populations.

Chemokines

Chemokines are a family of small cytokines, or signaling proteins secreted by cells. Their name is derived from their ability to induce directed chemotaxis in nearby responsive cells; they are chemotactic cytokines. These proteins have historically been known under several other names including the SIS family of cytokines, SIG family of cytokines, SCY family of cytokines, Platelet factor-4 superfamily or intercrines. Some chemokines are considered pro-inflammatory and can be induced during an immune response to recruit cells of the immune system to a site of infection, while others are considered homeostatic and are involved in controlling the migration of cells during normal processes of tissue maintenance or development. Chemokines are found in all vertebrates, some viruses and some bacteria, but none have been described for other invertebrates. All of these proteins exert their biological effects by interacting with G protein-linked transmembrane receptors called chemokine receptors, that are selectively found on the surfaces of their target cells.

The major role of chemokines is to act as a chemoattractant to guide the migration of cells. Cells that are attracted by chemokines follow a signal of increasing chemokine concentration towards the source of the chemokine. Some chemokines control cells of the immune system during processes of immune surveillance, such as directing lymphocytes to the lymph nodes so they can screen for invasion of pathogens by interacting with antigen-presenting cells residing in these tissues. These are known as homeostatic chemokines and are produced and secreted without any need to stimulate their source cell(s). Some chemokines have roles in development; they promote angiogenesis (the growth of new blood vessels), or guide cells to tissues that provide specific signals critical for cellular maturation. Other chemokines are inflammatory and are released from a wide variety of cells in response to bacterial infection, viruses and agents that cause physical damage such as silica or the urate crystals that occur in gout. Their release is often stimulated by pro-inflammatory cytokines such as interleukin 1. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. They are released by many different cell types and serve to guide cells of both innate immune system and adaptive immune system.

Functionally, chemokines are divided into two groups:
1. Homeostatic chemokines: are constitutively produced in certain tissues and are responsible for basal leukocyte migration. These include: CCL14, CCL19, CCL20, CCL21, CCL25, CCL27, CXCL12 and CXCL13. This classification is not strict; for example, CCL20 can act also as pro-inflammatory chemokine.
2. Inflammatory chemokines: these are formed under pathological conditions (on pro-inflammatory stimuli, such as IL-1, TNF-alpha, LPS, or viruses) and actively participate in the inflammatory response attracting immune cells to the site of inflammation. Examples include: CXCL8, CCL2, CCL3, CCL4, CCL5, CCL11, CXCL10.

Inflammatory chemokines are useful in the methods of the present invention. They are produced in high concentrations during infection or injury and determine the migration of inflammatory leukocytes into the damaged area. Typical inflammatory chemokines include: CCL2, CCL3 and CCL5, CXCL1, CXCL2 and CXCL8.

Chemokines are also characterized by the types of cells attracted:
1. Monocytes/macrophages: These are chemokines that attract monocytes and macrophages to the site of inflammation and include, but are not limited to, chemokines listed in Table 1.
2. Neutrophils: These chemokines are chemoattractants for neutrophils and also activate their metabolic and degranulation. They include, but are not limited to, chemokines listed in Table 2.
3. T-lymphocytes: The four key chemokines that are involved in the recruitment of T-lymphocytes to the site of inflammation are: CCL2, CCL1, CCL22 and CCL17. Furthermore, CXCR3 expression by T-cells is induced following T-cell activation and activated T-cells are attracted to sites of inflammation where the IFN-y inducible chemokines CXCL9, CXCL10 and CXCL11 are secreted.
4. Mast cells: On their surface, mast cells express several receptors for chemokines: CCR1, CCR2, CCR3, CCR4, CCR5, CXCR2, and CXCR4. Ligands of these receptors CCL2 and CCL5 play an important role in mast cell recruitment and activation in the lung. There is also evidence that CXCL8 might be inhibitory of mast cells.
5. Eosinophils: The migration of eosinophils into various tissues involved several chemokines of CC family: CCL11, CCL24, CCL26, CCL5, CCL7, CCL13, and CCL3. Chemokines CCL11 (eotaxin) and CCL5 (RANTES) act through a specific receptor CCR3 on the surface of eosinophils, and eotaxin plays an essential role in the initial recruitment of eosinophils into the lesion.

TABLE 1

Chemokines that attract monocytes and macrophages

| Chemokine | Receptor(s) |
|---|---|
| CXCL4 | CXCR3 |
| CXCL10 | CXCR3 |
| CXCL17 | ? |
| CX3CL1 | CX3CR1 |
| CCL1 | CCR8 |
| CCL2 | CCR2, CCR4 |
| CCL3 (CCL3L1) | CCR1, CCR4, CCR5 |
| CCL4 (CCL4L1) | CCR5 |
| CCL5 | CCR1, CCR3, CCR4, CCR5 |
| CCL6 | CCR1 |
| CCL7 | CCR1, CCR2, CCR3 |
| CCL8 | CCR1, CCR2, CCR3, CCR5 |
| CCL12 | CCR2 |
| CCL13 | CCR1, CCR2, CCR3 |
| CCL14 | CCR1, CCR3, CCR5 |
| CCL15 | CCR1, CCR3 |
| CCL16 | CCR1 |
| CCL22 | CCR4 |
| CCL23 | CCR1 |

TABLE 2

Chemokines that attract neutrophils

| Chemokine | Receptor |
|---|---|
| CXCL1 | CXCR1, CXCR2 |
| CXCL2 | CXCR1, CXCR2 |
| CXCL3 | CXCR2 |
| CXCL4 | CXCR3 |
| CXCL5 | CXCR2 |
| CXCL6 | CXCR1, CXCR2 |
| CXCL7 | CXCR1, CXCR2 |
| CXCL8 | CXCR1, CXCR2 |
| CXCL15 | ? |
| CCL9 | CCR1 |

TABLE 2-continued

Chemokines that attract neutrophils

| Chemokine | Receptor |
|---|---|
| CCL10 | CCR1 |
| CCL20 | CCR6 |
| CCL23 | CCR1 |
| CCL24 | CCR3 |

Chemokines are also characterized by their structures. Members of the chemokine family are divided into four groups depending on the spacing of their first two cysteine residues. Thus the nomenclature for chemokines is, for example, CCL1 for the ligand 1 of the CC-family of chemokines, and CCR1 for its respective receptor.
1. CC chemokines: The CC chemokine (or β-chemokine) proteins have two adjacent cysteines (amino acids), near their amino terminus. There have been at least 27 distinct members of this subgroup reported for mammals, called CC chemokine ligands (CCL-1 to CCL-28); CCL10 is the same as CCL9. Chemokines of this subfamily usually contain four cysteines (C4-CC chemokines), but a small number of CC chemokines possess six cysteines (C6-CC chemokines). C6-CC chemokines include CCL1, CCL15, CCL21, CCL23 and CCL28. CC chemokines induce the migration of monocytes and other cell types such as NK cells and dendritic cells.
   Examples of CC chemokine include monocyte chemoattractant protein-1 (MCP-1 or CCL2) which induces monocytes to leave the bloodstream and enter the surrounding tissue to become tissue macrophages.
2. CXC chemokines: The two N-terminal cysteines of CXC chemokines (or α-chemokines) are separated by one amino acid, represented in this name with an "X". There have been 17 different CXC chemokines described in mammals, that are subdivided into two categories, those with a specific amino acid sequence (or motif) of glutamic acid-leucine-arginine (or ELR for short) immediately before the first cysteine of the CXC motif (ELR-positive), and those without an ELR motif (ELR-negative). ELR-positive CXC chemokines specifically induce the migration of neutrophils, and interact with chemokine receptors CXCR1 and CXCR2. An example of an ELR-positive CXC chemokine is interleukin-8 (IL-8), which induces neutrophils to leave the bloodstream and enter into the surrounding tissue. Other CXC chemokines that lack the ELR motif, such as CXCL13, tend to be chemoattractants for lymphocytes. CXC chemokines bind to CXC chemokine receptors, of which seven have been discovered to date, designated CXCR1-7.
3. C chemokines: The third group of chemokines is known as the C chemokines (or γ chemokines), and is unlike all other chemokines in that it has only two cysteines; one N-terminal cysteine and one cysteine downstream. Two chemokines have been described for this subgroup and are called XCL1 (lymphotactin-α) and XCL2 (lymphotactin-β).
4. $CX_3C$ chemokines: A fourth group has also been discovered with members having three amino acids between the two cysteines and is termed $CX_3C$ chemokine (or d-chemokines). The only $CX_3C$ chemokine discovered to date is called fractalkine (or $CX_3CL1$), It is both secreted and tethered to the surface of the cell that expresses it, thereby serving as both a chemoattractant and as an adhesion molecule.

Materials and Methods

Analysis of Surgical Patient Data

The American College of Surgeons (ACS) National Surgical Quality Improvement Program (NSQIP) Participant Use Data File (PUF) for 2015 was utilized in this study, 2015 being the most recent available dataset. The ACS NSQIP PUF is a HIPAA compliant file with no protected health information that was accessed after approval from ACS NSQIP. For 2015, there were over 885,000 operative cased from 603 hospitals. Trained nurses enter all data in the NSQIP database with the focus on quality improvement, therefore complications like dehiscence are less likely to be missed as would be expected in self reporting situations. All patients with a primary CPT code involving a laparotomy were included for analysis, regardless of emergent status. These patients were assessed for a dehiscence after a pneumonia based on the postoperative days reported. Age was compared based upon two groups: 18-40 and >65. This was done to have a buffer age range (41-64) that would show a true physiologic difference based upon age.

Mice

All animal studies were approved by the Brown University Institutional Animal Care and Use Committee and carried out in accordance with the Guide for the Care and Use of Animals of the National Institutes of Health. C57BL/6J mice were purchased from The Jackson Laboratory. B6.SJL-PtprcaPepcb/BoyJ (0045.1 congenic) mice were bred in-house. Male mice 8-12 weeks of age were used in all experiments.

Polyvinyl Alcohol Sponge Implantation

Polyvinyl alcohol (PVA) sponge implantation surgeries were performed under anesthesia and analgesia by ketamine and xylazine injection. Backs were shaved and cleaned with povidone-iodine solution and isopropyl alcohol. Six 1 cm×1 cm×0.3 cm sterile PVA sponges (Ivalon, PVA Unlimited, Inc.) were placed into subcutaneous pockets through a 2 cm midline dorsal incision under sterile conditions. The incision was closed with surgical clips.

Full-Thickness Tail Wounding

The tail was cleaned with povidone-iodine solution and isopropyl alcohol. A 1 cm×0.3 cm area of the skin was excised using a scalpel 0.5 cm from the base of the tail. The wound bed was covered with a spray barrier film (Cavilon, 3M). Wound area was measured using calipers. Length and width measurements were taken at the midpoints of the wound bed. Tail wound images were acquired from a fixed position using a 12-megapixel iSight camera and were analyzed using ImageJ (NIH). All measurements were done in a blinded fashion.

Pulmonary Infection with *Klebsiella oxytoca*

Mice under anesthesia and analgesia by ketamine (60-80 mg/kg) and xylazine (30-40 mg/kg) injection were administered $2 \times 10^7$ CFU *Klebsiella oxytoca* intranasally in a volume of 30 µL using a sterile saline vehicle. Infected mice were monitored daily for a minimum of three days, and every other day for the remainder of the experiment, Wound Fluid and Cell Isolation Mice were euthanized by $CO_2$ asphyxiation prior to sponge removal. For wound fluid collection, three sponges from each animal were placed in the barrel of a 5 mL syringe, which was placed in a tube and centrifuged. The three remaining sponges from each animal were placed in 1× HBSS medium (1% FCS/penicillin/streptomycin11 M Hepes) and cells were isolated using a Stomacher (Tekmar). Wound cells were washed with 1× HBSS medium and red blood cells lysed. Cell counts were obtained using a Moxi Z Automated Cell Counter (Orflo) or an AttuneNxT flow cytometer (ThermoFisher).

Plasma and Blood Cell Collection

Blood was collected retro-orbitally into heparinized tubes. Plasma was separated from blood cells by centrifugation in Wintrobe Tubes (CMSLabcraft). Leukocytes were contained within the buffy coat layer at the interface of plasma and red blood cells, Residual red blood cells in the buffy coat layer were removed by lysis.

Bronchoalveolar Lavage and Lung Cell Preparation

To collect bronchoalveolar lavage fluid (BALF), a BD Venflon IV catheter was inserted into the exposed trachea. The catheter was used to flush the bronchoalveolar space twice with 1 mL of sterile 1×PES. Cell-free supernatants were collected for cytokine analyses and protein content quantification. Cells were counted with a Moxi Z Automated Cell Counter (Orflo) or an Attune NxT Flow Cytometer, and used in flow cytometry analyses.

To isolate cells from lung tissue, the right superior and middle lobes were perfused with 20 mL of PBS then cut into small pieces. The tissue was incubated for 45 min at 37° C. in 4 mL of DMEM containing type 4 collagenase (Worthington Biochemical Corporation) and DNAse I (Sigma-Aldrich). The digested lung tissue was passed through a 70 µM cell strainer to make a single cell suspension. After centrifugation the cell pellet was re-suspended in 4 mL of 40% Percoll/RPMI and carefully layered over 4 mL of 80% Percoll/PBS. The gradient was centrifuged at room temperature for 20 min at 600 xg with minimal acceleration and deceleration. Cells assembled in the interphase were collected, and washed with 10 mL RPMI media containing 5% fetal calf serum by centrifugation.

Pulmonary CFU Analysis

The right inferior lung lobe was homogenized in sterile 1× PBS. Serial dilutions of homogenates were plated onto Trypticase Soy Agar with 5% Sheep Blood (TSA II, BD) for quantitation of colony forming units (CFU).

Flow Cytometry Analysis of Cell Subsets

The following antibodies were used to identify cell subsets: Ly6C-FITC (AL-21, BD Biosciences), F4/80-APC eFluor60 (BM8, eBioscience), Siglec-F-PE or AR700 (E50-2440, ED Biosciences), CD11c-PE or BV711 (HL3, BioLegend), Ly6G-PerCP eFluor710 or V450 (1A8, eBioscience or ED Biosciences), CD45.2-APC/Fire750 or V450 (104, BioLegend or eBioscience), CD45.1-PE (A20, eBioscience), and CD11c-BV711 (N418, BioLegend). Dead cells were excluded from analyses using Fixable Viability Dye APC BV506 (eBioscience).

Surface staining: Cells were treated with anti-CD16/CD32 Fc receptor blocking antibody (clone 2.4G2) in 1× PBS (1% FBS) or 10 min on ice. Cells were then centrifuged and resuspended in 1× PBS (1% FBS) containing surface staining antibodies and incubated for 15 min on ice. Cells were washed with 1× PBS then incubated with Fixable Viability Dye diluted in 1× PBS for 15 min on ice. Cells were washed, then fixed with 1% paraformaldehyde for 15 min on ice.

Samples were acquired using an Attune NxT Acoustic Focusing Cytometer with Attune Software. Analyses were performed using FlowJo v10 software (Tree Star, Inc.). Gate placement was determined using isotype, FMO, or unstained control samples.

Cytokine Analysis

Cytokine concentrations were determined in wound fluid and plasma using a custom LEGENDplex bead-based immunoassay (BioLegend) according to manufacturer instructions. CXCL1 and CXCL5 concentrations were determined using DuoSet sandwich ELISA kits (R&D Systems) according to manufacturer instructions.

Bone Marrow Cell Adoptive Transfer

Femurs and tibias were collected from CD45.1 congenic mice in sterile 1× HBSS. Bone marrow was collected from femurs and tibias by flushing with sterile 1× HBSS medium (1% FCS/penicillin/streptomycin/1 M Hepes) using a syringe and red blood cells were lysed with water under sterile conditions. $5 \times 10^6$ cells in a volume of 100 µL of sterile 1× PBS were transferred retro-orbitally to recipient wild-type C57BL/6J mice.

Application of Exogenous Chemokines to Tail Wounds

Fibrin sealant (Tisseel, Baxter) was formed on the wound bed by co-application of thrombin and fibrinogen, which were prepared under sterile conditions according to the manufacturer instructions with the exception that the protease inhibitor component was omitted from the mixture. This was done to promote degradation of fibrin on the wound bed to facilitate chemokine release. Directly before application, recombinant murine CCL2 (Peprotech) and recombinant murine CXCL1 (Peprotech) were mixed into the fibrinogen component. Control mice were treated with Tisseel without chemokines. The fibrinogen and thrombin components were maintained at 37° C. to avoid polymerization. Using two pipets, equal volumes of fibrinogen and thrombin were simultaneously applied to the wound beds of anesthetized mice and allowed to polymerize. Treatments were given every day from wound days 1 to 7, then every other day for the remainder of the experiment. Each chemokine treatment contained 10 ng of recombinant CCL2 and 10 ng of recombinant CXCL1. Application volumes were adjusted according to wound bed area and ranged from 30 µL to 10 µL.

Application of Exogenous Chemokines to PVA Sponge Wounds

Recombinant murine CCL2 (Peprtotech) and recombinant murine CXCL1 (Peprotech) were diluted in 1× PBS for injection into implanted PVA sponges. The backs of mice were cleaned with iodine solution and isopropyl alcohol. 0.5 µg of each chemokine mixed in a total volume of 50 µL of PBS was injected through the skin and into the center of each sponge for a total treatment of 3 µg per wound. Control mice received injections of PBS vehicle. Mice were injected on wound days 5 and 6, and sponges were isolated on wound day 7.

Statistical Analysis

Biostatistical analyses of murine samples were carried out using the GraphPad Prism software package. For comparison of two groups the nonparametric Mann Whitney test was used. To compare 3 or more groups, the Kruskal-Wallis one-way analysis of variance or, for data sets with multiple time points, a two-way analysis of variance with Tukey's multiple comparisons test were used. All the groups were compared to each other. Unless otherwise noted, statistically significant changes between control and wound+*K. oxytoca* are denoted by *, between wound and wound+*K. oxytoca* are denoted by %, and between *K. oxytoca* and wound+*K. oxytoca* are denoted by #.

Clinical data were managed and analyzed using SAS (Cary, NC) using the included generalized linear mixed model and alpha was set to 0.05.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. Although methods and materials similar or equivalent to those described herein can be used in the practice or testing of this disclosure, suitable methods and materials are described below.

EXAMPLES

The invention now being generally described, it will be more readily understood by reference to the following examples which are included merely for purposes of illustration of certain aspects and embodiments of the present invention, and are not intended to limit the invention.

Example 1 Pneumonia is Associated with Wound Dehiscence Among Patients with Abdominal Incisions While it is well known that pneumonia is a risk of hospitalization, especially in post-surgery and trauma patients, it is not known how pneumonia impacts the ability to heal a wound.[23,24,26,28,35] To examine this question, we used the American College of Surgeons National Surgical Quality Improvement Program (NSQIP) Participant Use Data File (PUF) to assess the rate of abdominal incision dehiscence among patients with or without pneumonia.

Dehiscence is a post-surgical complication in which the wound ruptures along the site of the incision, and a clear indicator of a poorly healing surgical wound. Of over 885,000 cases in the ACS NSQIP PUF for 2015, 89,608 cases were included as they had a midline abdominal incision. A total of 1221 patients had a dehiscence (1.4%). When assessing patients who had a dehiscence and pneumonia, the dehiscence rate was 3.2%, compared to a dehiscence rate of 1.3% among patients who did not have pneumonia (P<0.0001, Table 3). Surgical site infection is typically associated with increased risk of dehiscence. Pneumonia did not make it more or less likely to have a surgical site infection (6.3% vs 67%, p=0.2829, Table 4). Age has also been associated with increased dehiscence. In a model to predict dehiscence, both age >65 (F=8.4, p=0.00037) and pneumonia (F=59.57, p<0.0001) were significant, but the interaction between the two was not (F=0.51, p=0.4749).

This analysis demonstrates that the onset of pneumonia in patients with surgical injuries is a risk factor for complications in wound healing.

TABLE 3

Rate of abdominal wound dehiscence among surgical patients with pneumonia

| PNEUMONIA | DEHISCENCE | | |
|---|---|---|---|
| | No Dehiscence (% of Total*) | Dehiscence (% of Total#) | TOTAL |
| No Pneumonia | 84,774 (98.72%) | 1,103 (1.28%) | 85,877 |
| Pneumonia | 3,613 (96.84%) | 118 (3.16%) | 3,731 |

*Percent of total number of patients in "No Pneumonia" group
Percent of total number of patients in "Pneumonia" group

TABLE 4

Rate of surgical site infection among surgical patients with or without pneumonia

| PNEUMONIA | Surgical Site Infection | | |
|---|---|---|---|
| | No Infection | Infection | TOTAL |
| No Pneumonia | 80,464 (93.7%) | 5,412 (6.30%) | 85,877 |
| Pneumonia | 3,479 (93.2%) | 252 (6.75%) | 3,731 |
| TOTAL | 83,943 | 5,665 | 89,608 |

Example 2 Acute Wound Healing Responses are Impaired in Mice with Co-Occurring Dermal Wounds and Lung Infections Activation of the innate immune system is an essential part of the early stages of wound healing. To investigate the effects of pulmonary infection on the inflammatory wound healing response, C57BL/6J mice were wounded by the dorsal subcutaneous implantation of polyvinyl alcohol (PVA) sponges. This model follows the acute stages of wound healing, and allows for the retrieval of cells and fluids from the implanted sponges after removal. [2,3,8,12,39]

To assess the rate of wound closure, a 1 cm×03 cm excisional skin wound was performed 0.5 cm from the base of the tail. These wounds heal primarily through reepithelization, and present a better model for human wound healing than mouse skin punch biopsies, which have a faster rate of closure and heal primarily through contraction.[36,37] Initial wound area measurements were obtained on day 1 post wounding. At this time, mice either remained uninfected or were infected intranasally with 2×10$^7$ CFU of the opportunistic pathogen *Klebsiella oxytoca* (wound+*K. oxytoca*).[38] The wound area was measured over the course of 15 days, and closure was determined by calculating wound size as a fraction of the day 1 wound area (FIG. 1a). Beginning at 7 days post-wounding, wound+*K. oxytoca* mice had significantly larger wounds compared to wounded mice, and wound healing was delayed at all subsequent time points (FIG. 1, FIG. 6a).

These results indicate that pulmonary infection causes a delay in wound closure.

Example 3 Pulmonary *K. oxytoca* Infection Resulted in Decreased Innate Leukocyte Cellularity in the Wound Activation of the innate immune system is an essential part of the early stages of wound healing. To investigate the effects of pulmonary infection on the inflammatory wound healing response, C57BL/6J mice were wounded by the dorsal subcutaneous implantation of polyvinyl alcohol (PVA) sponges. This model follows the acute stages of wound healing, and allows for the retrieval of cells and fluids from the implanted sponges after removal.[2,3,8,12,39]

The PVA sponge wound model was used to assess the effects of pulmonary infection on cellular wound healing responses. Sponges were implanted on wound day 0, and mice were uninfected or infected intranasally with *K. oxytoca* on wound day 5. A schematic is shown in FIG. 1c. Wound cellular content was decreased on wound day 6 and day 7 in infected mice compared to uninfected mice (FIG. 1d). Flow cytometry analysis of day 7 wounds shows the frequency of Ly6G$^+$ neutrophils (i), Siglec-F$^+$ eosinophils (ii), F4/80$^+$ monocytes/macrophages (iii), F4/80$^+$Ly6C$^{hi}$ monocytes (iv), and F4/80$^+$Ly6C$^{low}$ macrophages (v) on wound day 7. The absolute number of innate leukocyte populations in day 6 and day 7 wounds is shown in FIG. 1f. A panel of proinflammatory cytokines and chemokines were assayed in day 7 wound fluids using a flow cytometry-based multiplex bead array or ELISA including cytokines TNF-α, IL-6, and IL-1α (FIG. 1g) and chemokines CCL2, CCL3, CXCL10, CXCL1, and CXCL5 (FIG. 1h).

Figure 6:
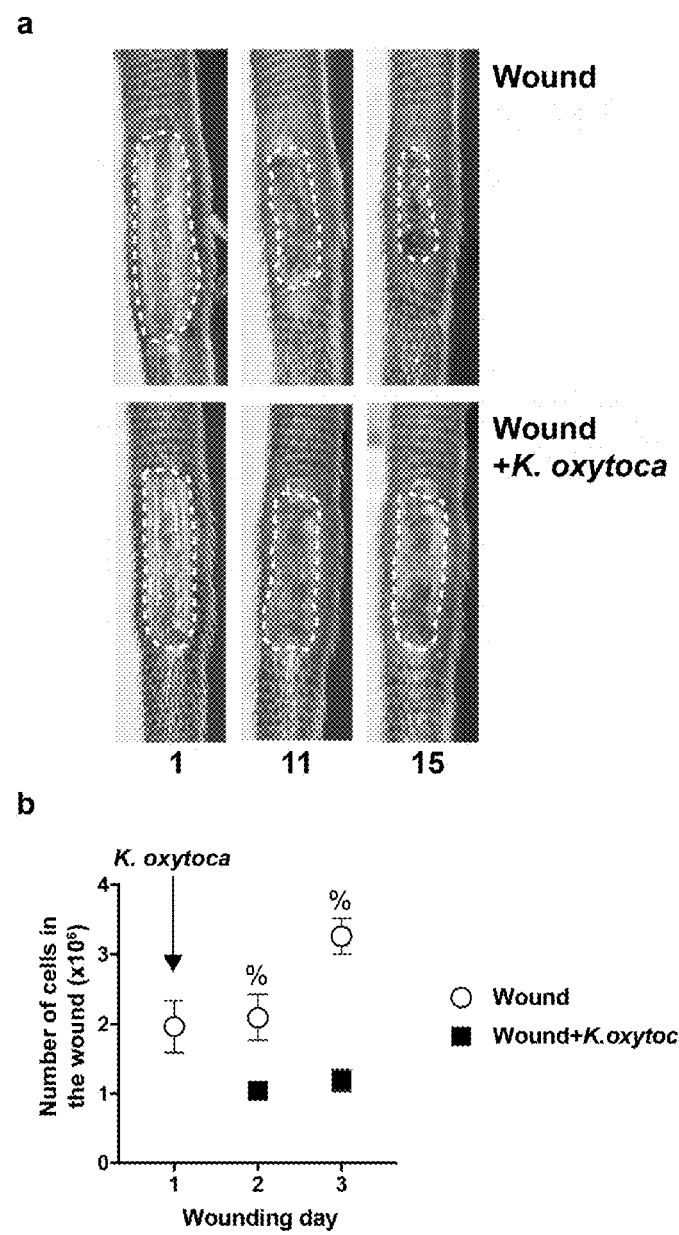
FIG. 6 shows the effect of pulmonary K. oxytoca infection on excisional tail wound closure in mice, FIG. 6a provides enlarged representative images of excisional tail wounds from uninfected control mice (top) or mice with pulmonary K. oxytoca infection (bottom) on wound days 1, 11, and 15 are shown, with wound margins traced for clarity.

Beginning at 7 days post-wounding, wound+*K. oxytoca* mice had significantly larger excisional tail wounds compared to wounded mice, and wound healing was delayed at all subsequent time points (FIG. 1b, FIG. 6). FIG. 6a provides enlarged representative images of excisional tail wounds from uninfected control mice (top) or mice with pulmonary *K. oxytoca* infection (bottom) on wound days 1, 11, and 15 are shown, with wound margins traced for clarity. FIG. 6b shows that pulmonary *K. oxytoca* infection causes reduced wound cellularity in PVA sponge wounds at early wound time points.

Figure 7:
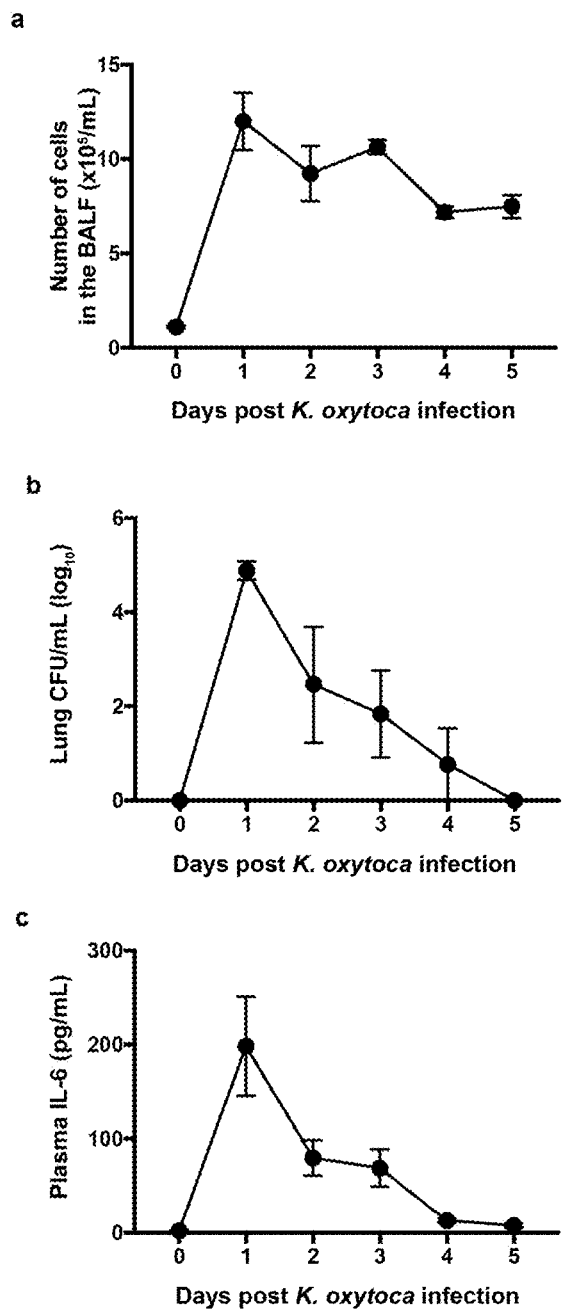
FIG. 7 shows the time course of pulmonary K. oxytoca infection. The kinetics of BALF cellularity (FIG. 7a), lung bacterial titers (FIG. 7b), and plasma IL-6 concentration (FIG. 7c) demonstrate the course of infection and inflammation in mice infected intranasally with 3×10$^7$ CFU K. oxytoca. The peak response occurs one day after infection for all parameters.

By 7 days post-sponge implantation, a large number of leukocytes are recoverable from implanted sponges, and the cytokine milieu reflects the transition from the inflammatory to the repair phases of wound healing.[2,3,8,12,39] Mice with PVA sponge wounds remained uninfected or were infected intranasally with *K. oxytoca* (wound+*K. oxytoca*) five days after sponge implantation in order to synchronize the inflammatory response to infection with the time of peak innate immune leukocyte infiltration into the PVA sponge wound[2] (FIG. 7).

The wound leukocyte milieu in uninfected and *K. oxytoca*-infected mice was assessed to determine whether pulmonary infection altered a specific cell type in the wound. Mice were wounded by PVA sponge implantation, and a cohort was infected intranasally with *K. oxytoca* on wound day 5 (FIG. 1c). Cell populations in the wound were identified by flow cytometry analysis on wound days 6 and 7. CD45$^+$ innate leukocytes are the predominant cell type in PVA sponge wounds at these times, and consist primarily of Ly6G+neutrophils, Siglec-F$^+$ eosinophils, F4/80$^+$Ly6C$^{hi}$ monocytes, and F4/80$^+$Ly6C$^{low}$ monocyte-derived macrophages.[2,3,12] At both time points, fewer infiltrating immune cells were isolated from sponges removed from wound+*K. oxytoca* mice compared to wounded mice alone (FIG. 1d).

Figure 8:
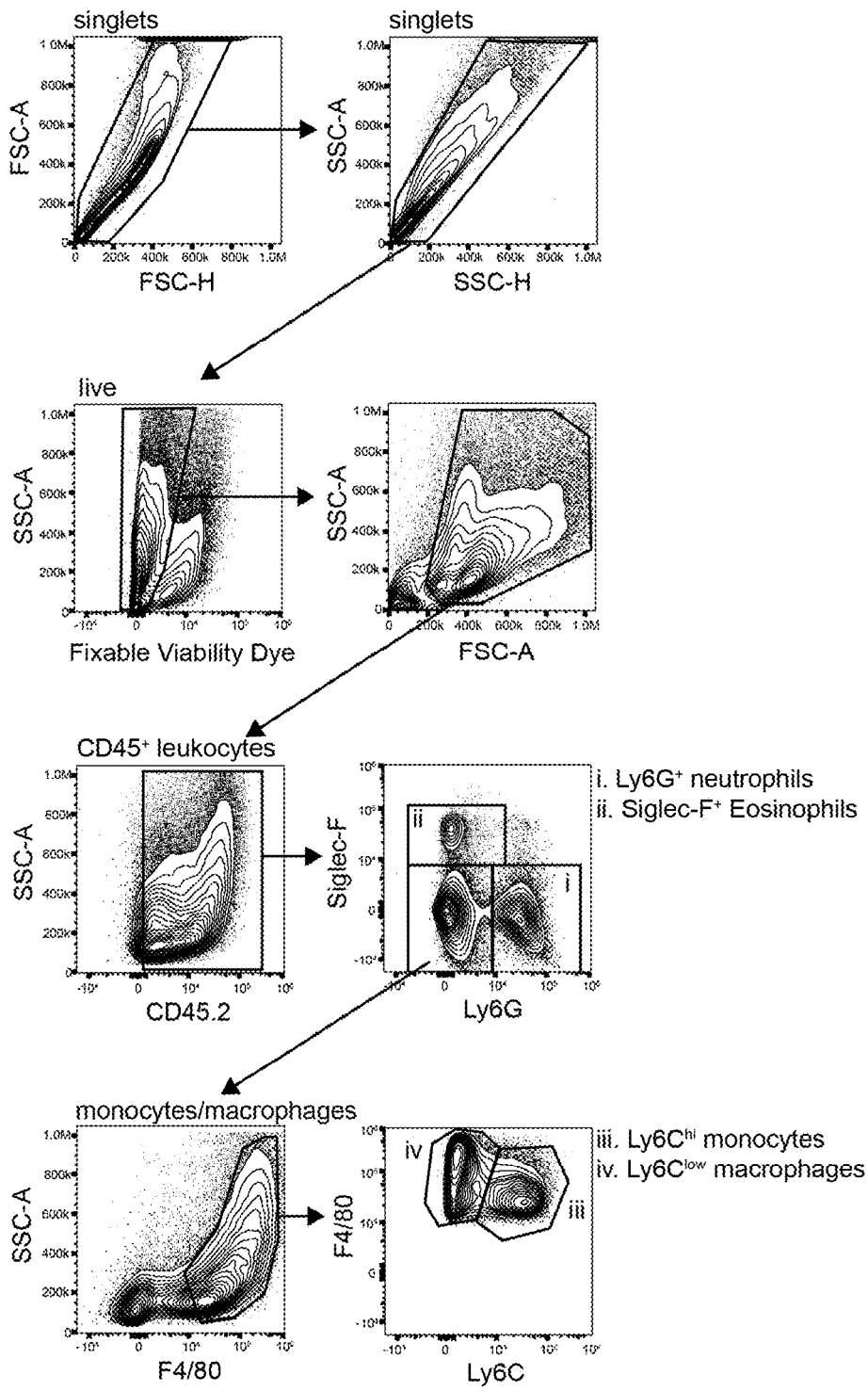
FIG. 8 shows a representative flow cytometry gating strategy to identify wound innate leukocytes. The following base gating strategy was employed to quantify innate leukocytes in the wound. Following doublet exclusion, dead cells were removed from analysis using a fixable viability dye. Cell debris and residual red blood cells were excluded by size using the FSC-A and SSC-A parameters. Hematopoietic cells were identified as CD45.2$^+$. Neutrophils (FIG. 8i) were identified as Ly6G$^+$Siglec-F$^-$. Eosinophils (FIG. 8ii) were identified as Siglec-F$^+$Ly6G$^-$. F4/80$^+$ monocytes/macrophages were gated from the Ly6G-Siglec-F- population. F4/80$^+$ cells were fractionated into Ly6C$^{hi}$ monocytes (FIG. 8iii) and Ly6C$^{low}$ macrophages (FIG. 8iv).

Representative flow cytometry gating for wound day 7 is shown in FIG. 1, and the full gating strategy to identify these cell populations is reported in FIG. 8. The relative percentage of neutrophils, monocytes, macrophages, and eosinophils was the same in wound and wound+$K.$ $oxytoca$ groups (FIG. 1). In contrast, the absolute number of all innate leukocyte populations examined, except for F4/80$^+$Ly6C$^{low}$ macrophages, was lower in wound+$K.$ $oxytoca$ mice than wounded mice alone (FIG. 1$f$).

Together, these data demonstrate that pulmonary infection suppresses the accumulation of innate leukocytes in the wound, which results in an overall loss of wound cellularity.

Example 4 Wound Cytokines and Chemokines are Suppressed in $K.$ $oxytoca$-Infected Mice Coordinated wound cytokine and chemokine responses are necessary for the normal progression of the repair response.[2-4,8,9,39,40] The effect of pulmonary infection on wound inflammatory cytokine and chemokine concentrations was assessed in wound fluids.

Mice were wounded by PVA sponge implantation and a subset was infected intranasally with $K.$ $oxytoca$ on wound day 5 (FIG. 1$c$). Wound fluid cytokine concentrations were measured on wound days 6 and 7.

As expected, the cytokines TNF-$\alpha$, IL-6, and IL-1$\alpha$, as well as the neutrophil chemoattractants CXCL1 and CXCL5, and the monocyte chemoattractants CXCL10, CCL2, and CCL3, were induced during the early inflammatory phase of acute wound healing. All of these cytokines and chemokines were significantly reduced in the wound fluids of wound+$K.$ $oxytoca$ mice compared to wounded mice alone at both time points examined (FIG. 1$g$ and FIG. 1$h$).

These data suggest that pulmonary infection causes suppression of cytokine and chemokine responses in PVA sponge wounds.

Example 5 the Pulmonary Cellular Response and Resistance to $K.$ $oxytoca$ Infection is Maintained in Mice with Wounds, Despite a Transient Suppression of BALF Cytokine Levels In response to $K.$ $oxytoca$ infection, inflammatory cytokines and chemokines are rapidly produced in the lung. To determine whether an ongoing wound healing response would influence the ability to respond to a pulmonary bacterial infection, cytokine levels in the BALF were assessed in control, wound, $K.$ $oxytoca$, or wound+$K.$ $oxytoca$ groups (FIG. 1$g$ and FIG. 1$h$).

Figure 2:
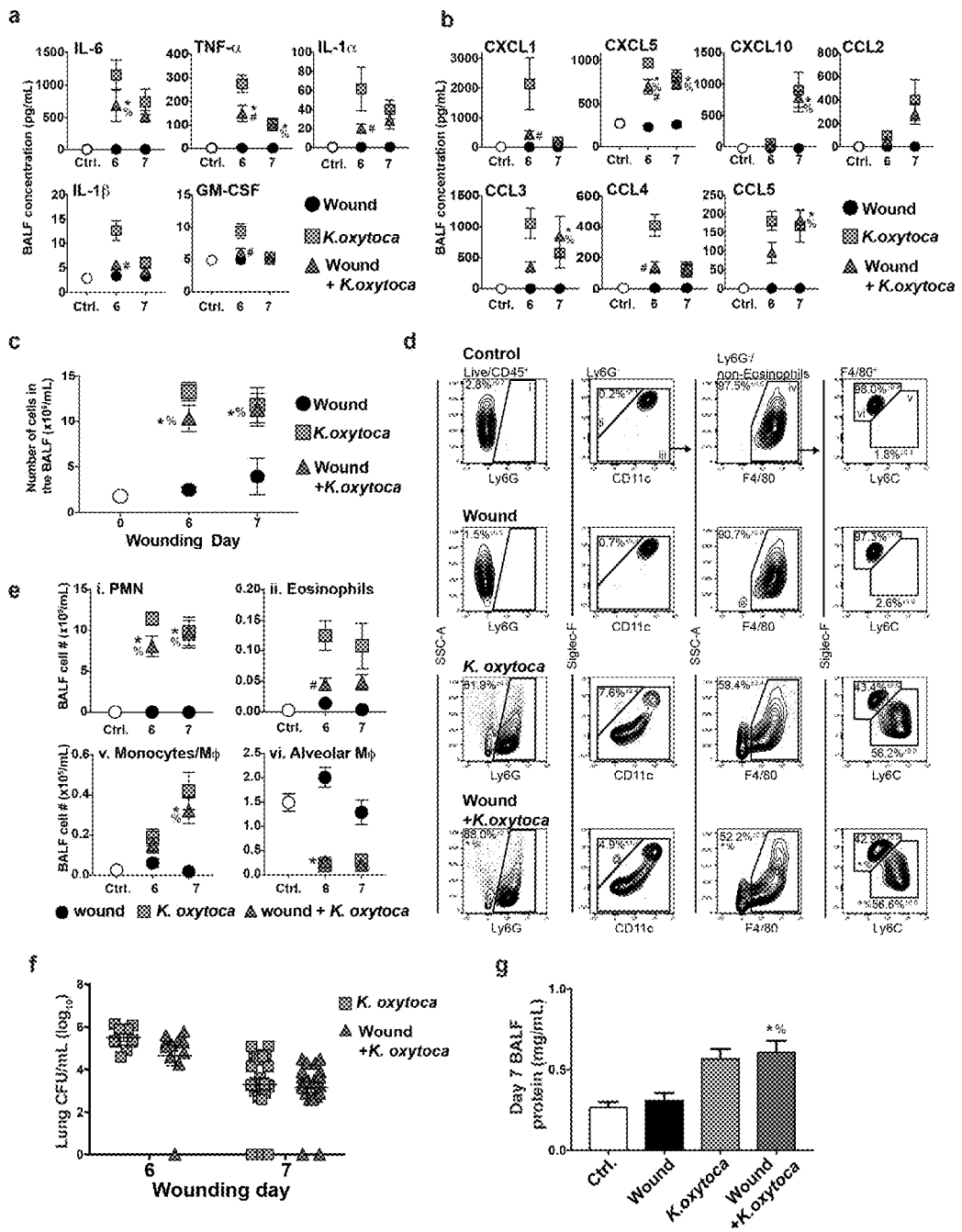
FIG. 2 shows that delayed pulmonary cytokine and innate leukocyte responses do not alter resistance to *K. oxytoca* infection. To determine the effect of distal cutaneous wounding on the pulmonary response to *K. oxytoca* infection, C57BL/6J mice were wounded by PVA sponge infection, then infected 5 days later as shown in FIG. 1c. Unwounded mice were additionally infected with *K. oxytoca* or remained uninfected as control. A panel of cytokines (FIG. 2a) and chemokines (FIG. 2b) that are induced in response to bacterial infection were measured in the bronchoalveolar lavage fluid (BALF). The effect of wounding on BALF cellular content was determined (FIG. 2c). The distribution of Ly6G$^+$ neutrophils (PMN, i), CD11c$^-$Siglec-F$^+$ eosinophils (ii), CD11c$^{+/-}$F4/80$^+$ monocytes/macrophages (mΦ) (iii and iv), F4/80$^+$Ly6C$^{hi}$Siglec-F$^-$ monocytes/macrophages (v), and F4/80$^+$Ly6C$^{low}$Siglec-F$^+$ alveolar macrophages (mΦ) (vi) in the BALF isolated from mice on wound day 7 was determined by flow cytometry analysis (FIG. 2d). The absolute number of these innate leukocyte populations was calculated on wound days 6 and 7 (FIG. 2e). Lung *K. oxytoca* titers were determined in infected mice with or without PVA sponge wounds on wound day 6 and day 7 (FIG. 2f). The BALF protein content was measured by BCA assay to assess effect of wounding and *K. oxytoca* infection on pulmonary vascular permeability (FIG. 2g). Data are shown as the mean ±SEM with a minimum n=10 mice per group from three independent experiments. Results are considered statistically significant when p≤0.05. Statistically significant changes between control and wound+*K. oxytoca* are denoted by *, between wound and wound+*K. oxytoca* are denoted by %, and between *K. oxytoca* and wound+*K. oxytoca* are denoted by #.

The concentrations of IL-6, TNF-$\alpha$, IL-la, IL-1p, and GM-CSF were measured in the BALF in all groups (FIG. 2$a$). $K.$ $oxytoca$ infection alone induced all cytokines as early as one day after infection (wound day 6), before the levels subsided on wound day 7. The production of TNF-$\alpha$, IL-1$\alpha$, IL-1p, and GM-CSF in wound+$K.$ $oxytoca$ mice was delayed compared to infected mice alone, suggesting that the presence of a distal cutaneous wound suppressed the initial cytokine response to pulmonary infection. A similar pattern was observed in the production of the neutrophil chemoattractants OXCL1 and CXCL5, as well as the myeloid and lymphocyte chemoattractant CCL4 (FIG. 2$b$).

To determine if the observed delay in pulmonary cytokine and chemokine production in the BALF of wound+$K.$ $oxytoca$ mice influenced the ability to respond to the bacterial pathogen, we compared the cellular pulmonary response to $K.$ $oxytoca$ infection between wounded and unwounded mice. Mice were wounded and/or infected as previously described (FIG. 1$c$).

Figure 9:
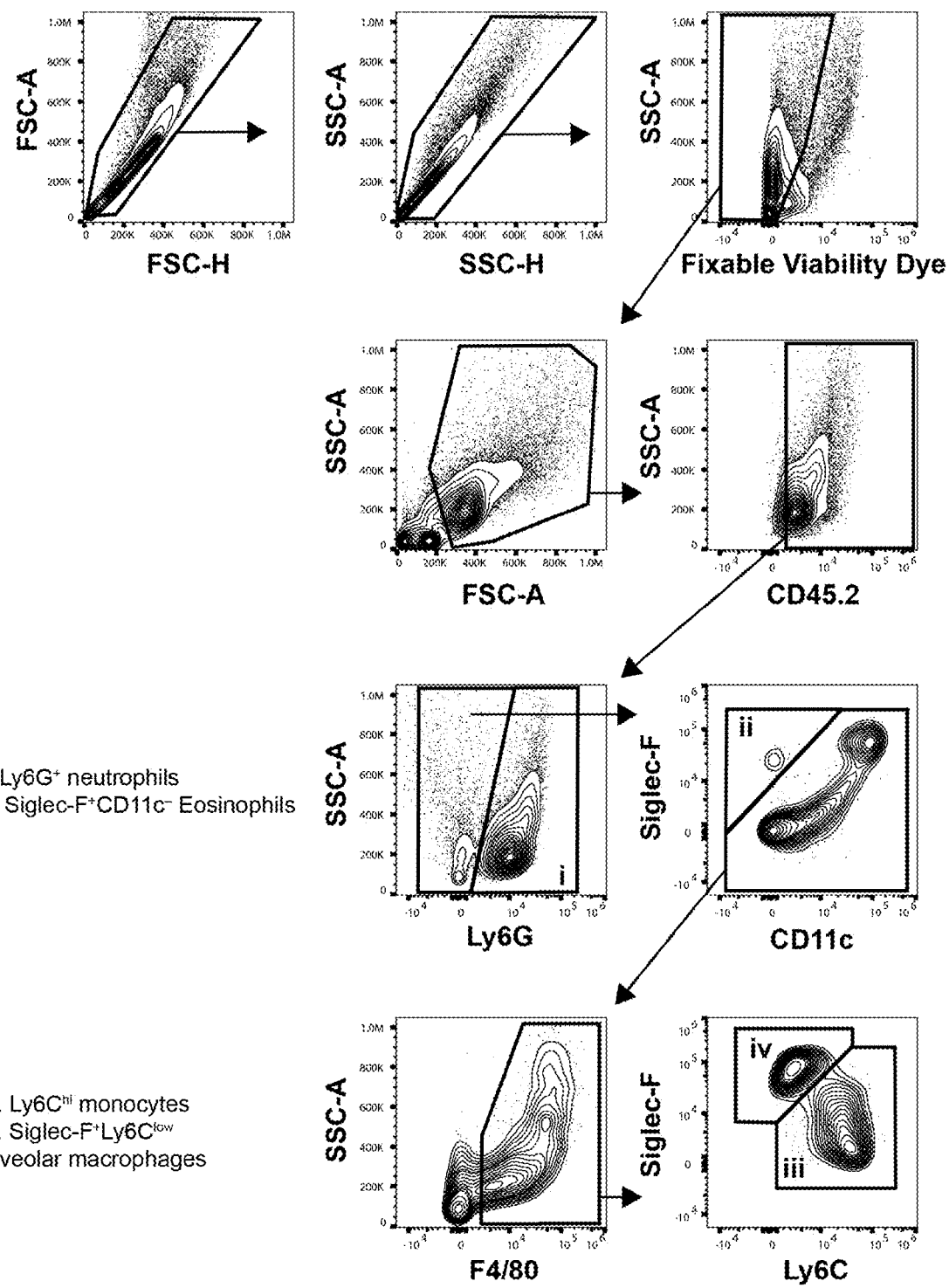
FIG. 9 shows a representative flow cytometry gating strategy to identify BALF innate leukocyte populations. This gating strategy was employed to quantify innate leukocytes in the BALF. Doublets were excluded, then dead cells were removed from the analysis using a fixable viability dye. Cell debris and residual red blood cells were excluded by size using the FSC-A and SSC-A parameters. Hematopoietic cells were identified as CD45.2$^+$. Neutrophils (FIG. 9i) were identified as Ly6G$^+$Siglec-F$^-$. Eosinophils (FIG. 9ii) were identified as Siglec-F$^+$CD11c$^-$Ly6G$^-$. F4/80$^+$ monocytes/macrophages were gated from the Ly6G-Siglec-F-populations. F4/800 cells were fractionated into Ly6C$^{hi}$ monocytes (FIG. 9iii) and Siglec-F$^+$Ly6C$^{low}$ alveolar macrophages (FIG. 5iv).

PVA sponge wounds did not affect the number of cells isolated from the BALF, while $K.$ $oxytoca$ infection caused an increase in BALF cellularity compared to control mice (FIG. 2$c$). The distribution of CD45$^+$ innate leukocytes in the BALF of control, wound, $K.$ $oxytoca$, and wound+$K.$ $oxytoca$ groups was determined on wound days 6 and 7 by flow cytometry analysis. Representative flow cytometry analyses from wound day 7 are shown in FIG. 2$d$, and the full BALF gating strategy is presented in FIG. 9. Nearly all cells isolated from the BALF of uninfected mice were F4/80$^+$Ly6C$^{low}$Siglec-F$^+$ alveolar macrophages, while Ly6G$^+$ neutrophils were the predominant innate leukocyte population in $K.$ $oxytoca$-infected mice. F4/80$^+$Siglec-F$^{low}$Ly6C$^{hi}$ monocytes/macrophages also accumulated in the BALF of infected mice. The presence of a PVA sponge wound did not affect the cellular makeup of the BALF (FIG. 2$e$), with the exception of Siglec-F$^+$CD11c$^-$ eosinophils. Eosinophils were a very small fraction of the overall BALF leukocyte milieu, however their numbers were decreased in the BALF of wound+$K.$ $oxytoca$ mice compared to $K.$ $oxytoca$-infected mice alone (FIG. 2$e$).

To determine if the presence of a PVA sponge wound impacted the ability to control to the pulmonary infection, bacterial titers were measured in $K.$ $oxytoca$, and wound+$K.$ $oxytoca$ groups. $K.$ $oxytoca$ titers were the same in infected mice with or without wounds (FIG. 2$f$). BALF protein content was also measured to assess pulmonary vascular permeability in control, wound, $K.$ $oxytoca$, and wound+$K.$ $oxytoca$ groups.

Infection caused an increase in BALF protein content, and this was not affected by the presence of a PVA sponge wound (FIG. 2$g$). Overall, despite a transient delay in cytokine and chemokine production in wound+$K.$ $oxytoca$ mice, these data suggest that the presence of a PVA sponge wound does not alter the ability to mount an innate cellular response in the lung or impact the early control of bacterial infection.

Example 6 Pulmonary Resistance to $S.$ $pneumoniae$ Infection is Maintained at the Expense of Wound Cellular and Cytokine Responses To determine whether the suppressive effect of $K.$ $oxytoca$ infection on dermal wound healing was pathogen-specific, or more broadly applicable to other bacterial pulmonary infections, the experiments described in FIG. 1$c$ were repeated using pulmonary infection with $Streptococcus$ $pneumoniae$. As infection with $S.$ $pneumoniae$ is lethal after several days, we focused on the innate immune wound healing response.

Similar to what was observed with $K.$ $oxytoca$ infection, wound cellularity was diminished in mice with $S.$ $pneumoniae$ infection, which corresponded to loss of neutrophils, monocytes, and macrophages. Wound fluid cytokine and chemokine levels were also reduced in mice with pulmonary $S.$ $pneumoniae$ infection. Conversely, pulmonary resistance to $S.$ $pneumoniae$ infection was not affected by the presence of a wound.

Figure 10:
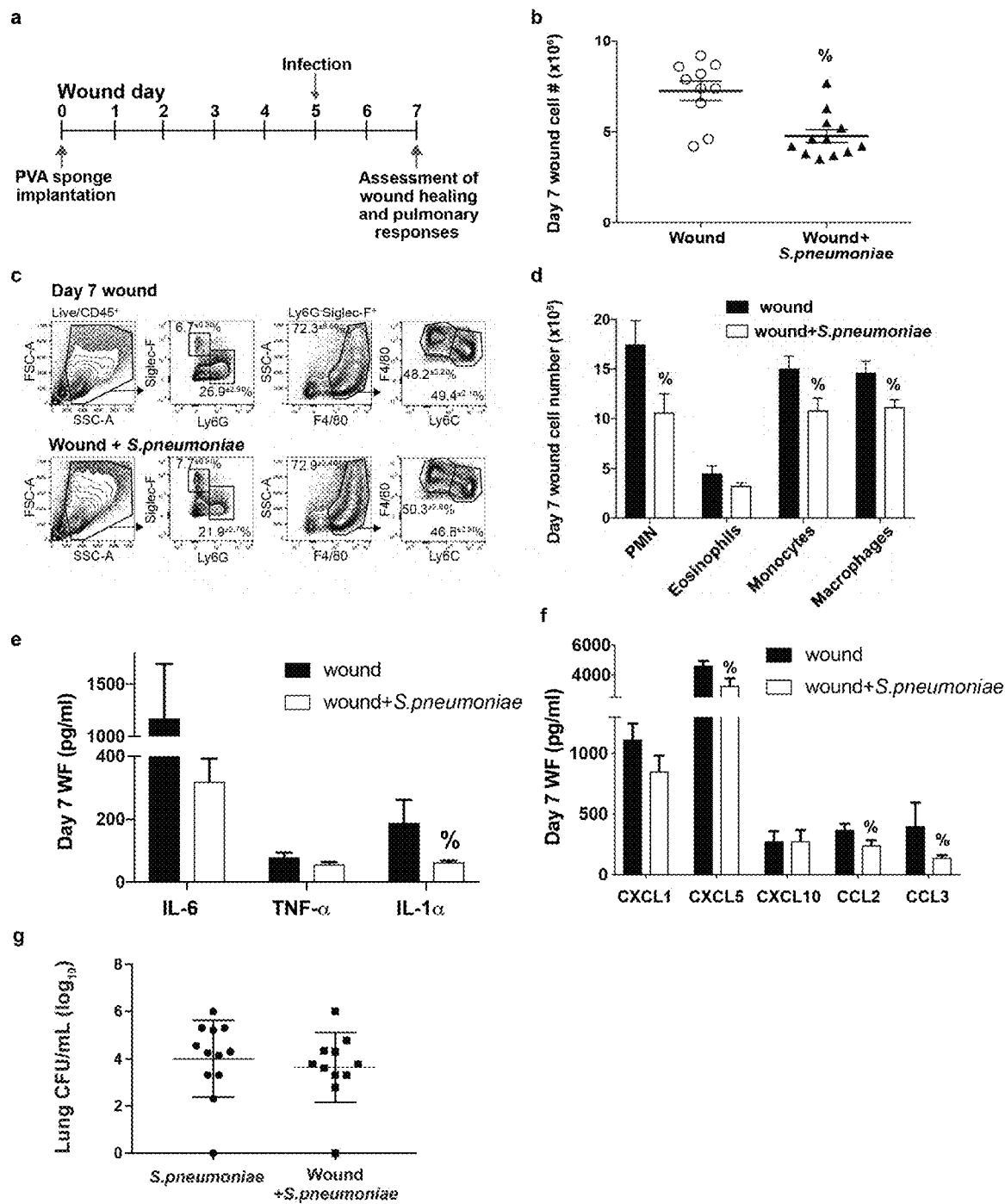
FIG. 10 shows the effect of pulmonary Streptococcus pneumoniae infection on cutaneous wound healing. Mice were wounded by the subcutaneous implantation of PVA sponges, then infected intranasally with 5×10$^6$ CFU S. pneumoniae 5 days later. Wound cellular and cytokine responses were assessed on wound day 7 (FIG. 10a). The onset of pulmonary S. pneumoniae infection suppressed the overall cellularity of the wound on day 7 (FIG. 10b). The proportion of innate leukocytes infiltrating the wound on day 7 was not altered by S. pneumoniae infection (FIG. 10c), although the absolute number of neutrophils, monocytes, and macrophages was suppressed by the pulmonary infection (FIG. 10d). The effect of pulmonary infection on wound fluid (WF) concentrations of the proinflammatory cytokines IL-6, TNF-α, and IL-1β (FIG. 10e) and the chemokines CXCL1, CXCL5, CXCL10, CCL2, and CCL3 (FIG. 10f) was determined. Prior wounding did not alter the lung bacterial burden as assessed on wound day 7 (FIG. 10g). Data are the mean ±SEM with a minimum n=10. % indicates p≤0.05 comparing wound+K. oxytoca to wound groups.

Together these results suggest that the prioritization of innate immune responses between wound healing and pulmonary infection is not pathogen-specific (FIG. 10).

Example 7 $K.$ $oxytoca$ Infection Alters Circulating Innate Leukocyte and Systemic Cytokine Responses in Wounded Mice The circulation is the immediate source of innate leukocytes involved in both wound healing and pulmonary antibacterial defense. Therefore, one potential explanation for the decreased cellularity and cytokine responses observed in the wounds of wound+*K. oxytoca* mice is suppression of the systemic immune response. The blood and plasma cellularity and cytokine responses were therefore examined in control, wound, *K. oxytoca*, and wound+*K. oxytoca* groups.

Figure 11:
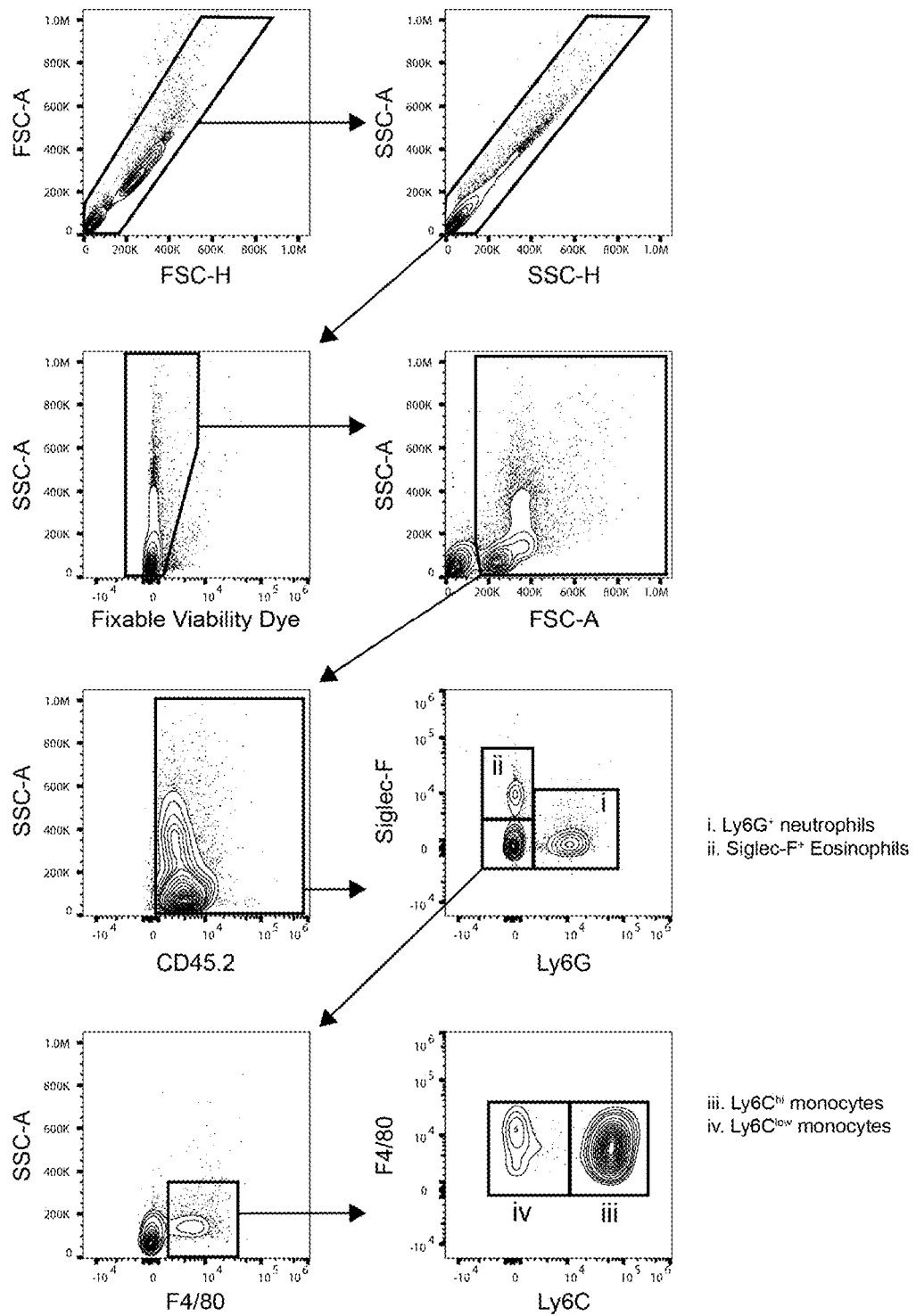
FIG. 11 shows a representative gating strategy to identify blood innate leukocyte populations. This gating strategy was employed to quantify innate leukocytes in the blood. Doublets were excluded, then dead cells were removed from the analysis using a fixable viability dye. Cell debris and residual red blood cells were excluded by size using the FSC-A and SSC-A parameters. Hematopoietic cells were identified as CD45.2$^+$. Neutrophils (FIG. 11i) were identified as Ly6G$^+$Siglec-F$^-$. Eosinophils (FIG. 11ii) were identified as Siglec-F$^+$CD11c$^-$Ly6G$^-$. F4/80$^+$ monocytes were gated from the Ly6G$^-$Siglec-F$^-$ population. F4/80 cells were fractionated into Ly6C$^{hi}$ inflammatory monocyte (FIG. 11iii) and Ly6C$^{low}$ patrolling monocyte populations (FIG. 11iv)

All three experimental groups had a decrease in the number of circulating cells at post-wound days 6 and 7 as compared to control mice, likely due to margination of cells to the inflamed peripheral sites (FIG. 3a). The distribution of innate leukocytes was examined by flow cytometry (FIG. 3b and FIG. 11). Overall, the distribution of circulating CD45+ innate leukocytes in wound+*K. oxytoca* mice followed the pattern observed in *K. oxytoca*-infected mice alone. Specifically, infection caused an increase in the frequency of Ly6G+ neutrophils and F4/80+Ly6C$^{hi}$ inflammatory monocytes, and a drop in the percentage of Siglec-F+ eosinophils and F4/80+Ly6C$^{low}$ monocytes. The frequency of these leukocyte subsets was not altered by the presence of a PVA sponge wound (FIG. 3b).

In contrast, calculating the total number of circulating leukocytes revealed some clear differences between the groups. Ly6G+ neutrophils were the most numerous circulating innate leukocyte population among those examined in all groups (FIG. 3c). In addition, wound+*K. oxytoca* mice had at least two-fold more circulating neutrophils than any other group (FIG. 3c). *K. oxytoca* and wound+*K. oxytoca* groups had fewer circulating Siglec-F+ eosinophils and Ly6C$^{hi}$ monocytes compared to control and wound groups (FIG. 3c). In contrast, the number of blood Ly6C$^{low}$ monocytes was similar in all groups over time (FIG. 3c). Together, these data demonstrate that the combination of a wound and pulmonary infection causes blood neutrophilia.

Systemic cytokine levels are important in the activation of immune cells. To assess whether competing insults altered the balance of systemic cytokines, the plasma concentration of inflammatory cytokines and chemokines was measured by ELISA or multiplex bead array. Mice were wounded by PVA sponge implantation and/or infected as described above (FIG. 1c). The concentration of IL-6 was low in the plasma from control and wounded mice, and was induced in *K. oxytoca* and wound+*K. oxytoca* groups. TNFα was also elevated systemically in mice infected with *K. oxytoca*, but the induction of TNFα was delayed in wound+*K. oxytoca* mice, similar to what was observed in the BALF. The concentration of IL-1α was highest in control and wounded mice, while the levels decreased in *K. oxytoca*-infected and wound+*K. oxytoca* mice. IL-1β and GM-CSF were not changed relative to control in all treatment groups (FIG. 3d).

Given the changes in cellularity of innate immune cells in the blood, we also determined the systemic levels of chemokines involved in innate leukocyte migration. The concentration of neutrophil chemoattractants CXCL1 and CXCL5 were measured in the plasma of control, wound, *K. oxytoca*, and wound+*K. oxytoca* groups.

The concentration of CXCL1 was low in control and wounded groups. CXCL1 was strongly induced by *K. oxytoca* infection at wound day 6. In contrast, the induction of CXCL1 was attenuated at this time point in wound+*K. oxytoca* mice. Plasma CXCL5 concentrations were the highest in wounded mice alone on wound day 6, and this peak was diminished in wound+*K. oxytoca* mice.

Figure 3:
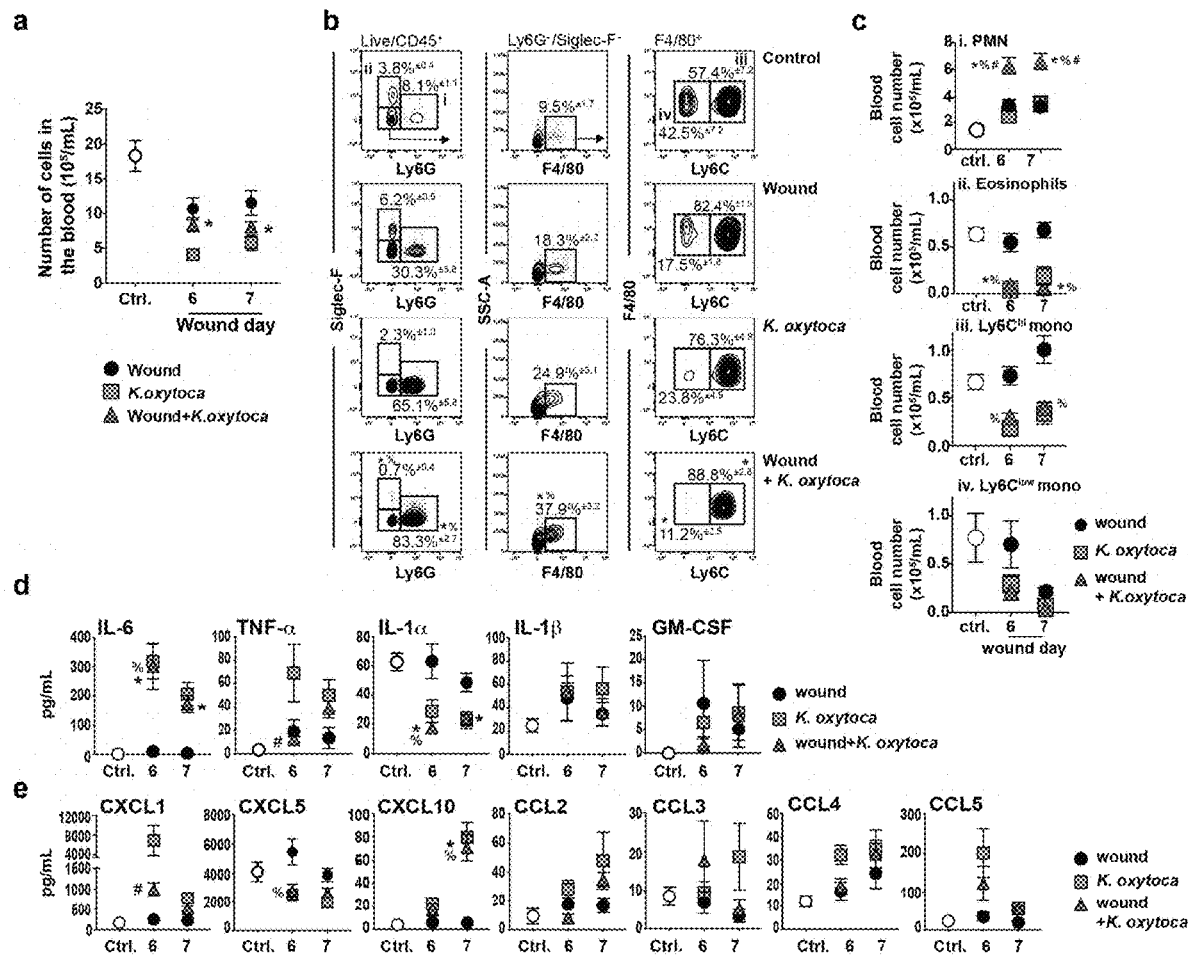
FIG. 3 shows that systemic cellular and cytokine responses are altered by wounding and pulmonary *K. oxytoca* infection. Blood cellularity and plasma cytokines/chemokines were assayed to determine the effect of wounding and/or lung bacterial infection on systemic innate immune responses. C57BL/6J mice were wounded by PVA sponge implantation and infected with *K. oxytoca* as shown in FIG. 1c. Blood cellularity was determined from control (uninfected+unwounded) mice and on wound day 6 and day 7 from *K. oxytoca*-infected, wounded, and wounded+infected mice (FIG. 3a). Flow cytometry analysis was used to determine the frequency of innate leukocyte subsets isolated from the blood on wound day 7, including Ly6G$^+$ neutrophils (PMN, i), Siglec-F$^+$ eosinophils (ii), F4/80 monocytes, F4/80$^+$Ly6C$^{hi}$ inflammatory monocytes (iii), and F4/80$^+$Ly6C$^{low}$ patrolling monocytes (iv) (FIG. 3b). The absolute number of circulating innate leukocytes from control and wound days 6 and 7 in shown in FIG. 3c. Plasma cytokines TNF-α, IL-6, and IL-1α (FIG. 3d) and chemokines CCL2, CCL3, CXCL10, CXCL1, and CXCL5 (FIG. 3e) were measured by multiplex bead array or ELISA. Data are shown as the mean ±SEM with minimum n=10 mice per group from three independent experiments. Results are considered statistically significant when p≤0.05. Statistically significant changes between control and wound+*K. oxytoca* are denoted by *, between wound and wound+*K. oxytoca* are denoted by %, and between *K. oxytoca* and wound+*K. oxytoca* are denoted by #.

Chemokines that direct the migration of other innate leukocytes such as inflammatory monocytes and eosinophils, including CXCL10, CCL2, CCL3, CCL4, and CCL5, were also measured. The concentration of these chemokines was not significantly altered in wound+*K. oxytoca* mice compared to either wounded or *K. oxytoca* mice alone (FIG. 3e). Taken together, these data suggest that wound+*K. oxytoca* mice may have a chemotactic signal dysregulation that alters neutrophil mobilization to the periphery (FIG. 3), while other innate leukocyte signals are largely unaffected.

Taken together, these data point to a chemotactic signal dysregulation in wound+*K. oxytoca* mice that alters neutrophil mobilization to the periphery (FIG. 3), while other innate leukocyte signals are largely unaffected.

Figure 4:
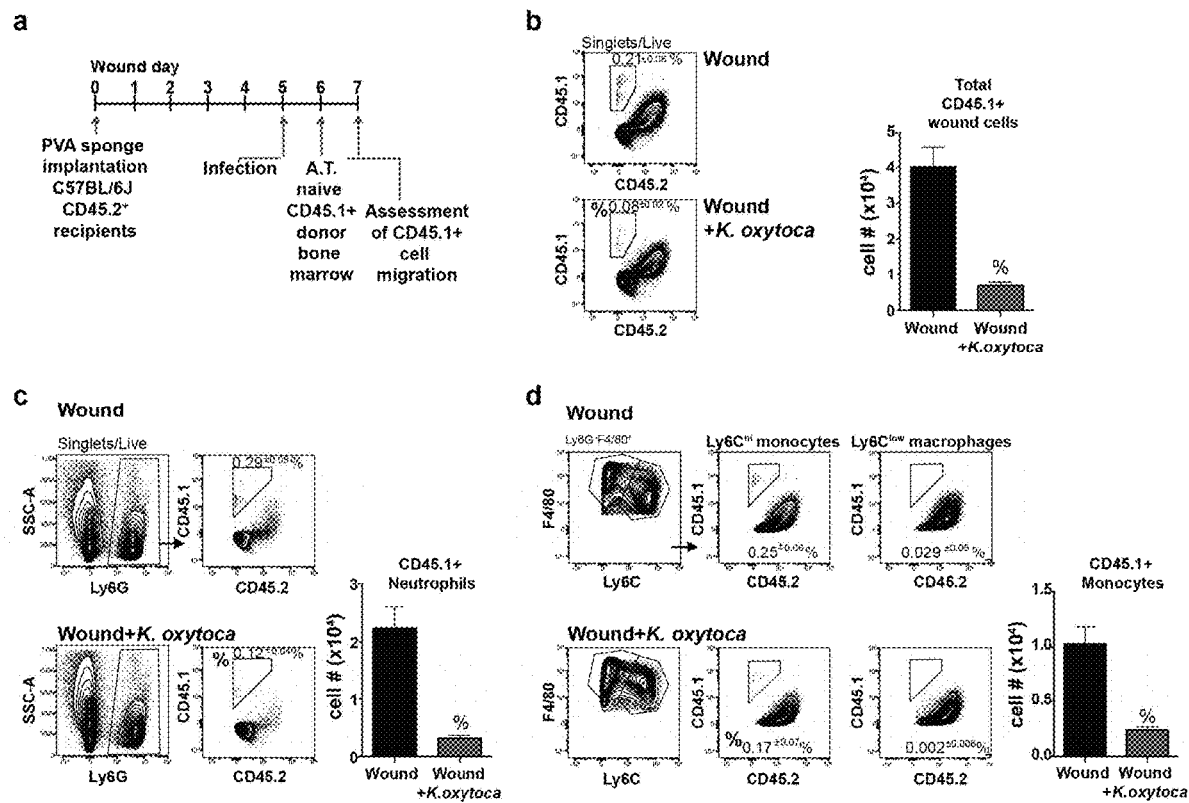
FIG. 4 shows that the neutrophil and monocyte trafficking to wounds is impaired in mice with pulmonary *K. oxytoca* infection. Naïve CD45.1$^+$ congenic bone marrow cells were adoptively transferred to uninfected or *K. oxytoca*-infected mice with PVA sponge wounds as depicted in FIG. 4a. The percentage and number of total donor-derived CD45.1$^+$ cells (FIG. 4b), CD45.1$^+$ Ly6G$^+$ neutrophils (FIG. 4c), CD45.1$^+$ F4/80$^+$Ly6C$^{hi}$ monocytes and CD45.1$^+$ F4/80$^+$Ly6C$^{low}$ macrophages (FIG. 4d) was determined the wounds of uninfected and *K. oxytoca*-infected mice by flow cytometry. Data are shown as the mean ±SEM with minimum n=12 mice per group from three independent experiments. Results are considered statistically significant when p≤0.05. Statisitcally significant changes between wound and wound+*K. oxytoca* are denoted by %.

Example 8 Fewer Leukocytes Migrate to the Wounds of Mice with Concurrent Pulmonary Infection The imbalance of chemokine concentrations between in the plasma and the wound fluids from wound+*K. oxytoca* mice suggested that innate leukocytes might lack the proper signals to traffic to the wound. To test this, a bone marrow cell adoptive transfer approach was taken. CD45.2 congenic C57BL/6J recipient mice were wounded by PVA sponge implantation, and a cohort was infected intranasally with *K. oxytoca* on wound day 5. On wound day 6, bone marrow cells from naive CD45.1 congenic mice were transferred intravenously to wound or wound+*K. oxytoca* CD45.2 congenic recipient mice (FIG. 4a). The fraction of CD45.1+ donor-derived cells in the wounds of recipient mice was assessed on wound day 7 by flow cytometry.

There were fewer CD45.1 donor-derived cells by proportion and total number in the wounds of wound+*K. oxytoca* mice as compared to the wounds of wounded recipient mice alone (FIG. 4b). Similarly, there were significantly fewer donor-derived CD45.1+ Ly6G+ neutrophils and F4/80+ Ly6C$^{hi}$ monocytes by proportion and absolute number in the wounds of wound+*K. oxytoca* recipient mice compared to wounded recipient mice alone (FIG. 4c and FIG. 4d). There was only a very small proportion (<0.05%) of CD45.1+F4/80+Ly6C$^{low}$ macrophages in recipient wounds (FIG. 4d). These were likely derived from monocytes that matured in situ after migrating from the circulation.[12]

Together, these data suggest that circulating neutrophils and inflammatory monocytes are impaired in their ability to migrate to wounds in mice with ongoing *K. oxytoca* infection.

Example 9 Inducing Innate Immune Cell Trafficking to Wounds with Exogenous CCL2 and CXCL1 Improves Healing Given the reduction in monocyte and neutrophil trafficking into wound+*K. oxytoca* mice, we hypothesized that restoring trafficking would improve wound healing responses in these mice. The PVA sponge implantation model was used to examine the effect of administering a monocyte chemoattractant protein, CCL2, and a neutrophil-activating protein, CXCL1, on wound innate leukocyte responses.

CCL2 is the chemokine (C-C motif) ligand 2 also referred to as monocyte chemoattractant protein 1 (MCP1) and small inducible cytokine A2. It is a small cytokine that belongs to the CC chemokine family, CCL2 recruits monocytes, memory T cells, and dendritic cells to the sites of inflammation produced by either tissue injury or infection.

CXCL1 is the chemokine (C-X-C motif) ligand 1 that was previously called CRO1 oncogene, GROα, KC, neutrophil-activating protein 3 (NAP-3) and melanoma growth stimulating activity, alpha (MGSA-α). It is a small cytokine belonging to the CXC chemokine family. CXCL1 is expressed by macrophages, neutrophils and epithelial cells,[57,58] and has neutrophil chemoattractant activity.[59,60]

Mice were wounded, and a subset was infected on wound day 5 with *K. oxytoca* as described above (FIG. 1c). Recombinant CCL2 and recombinant CXCL1 were injected into each sponge on wound days 5 and 6. For comparison, a cohort of mice received injections of PBS instead of chemokines.

Figure 5:
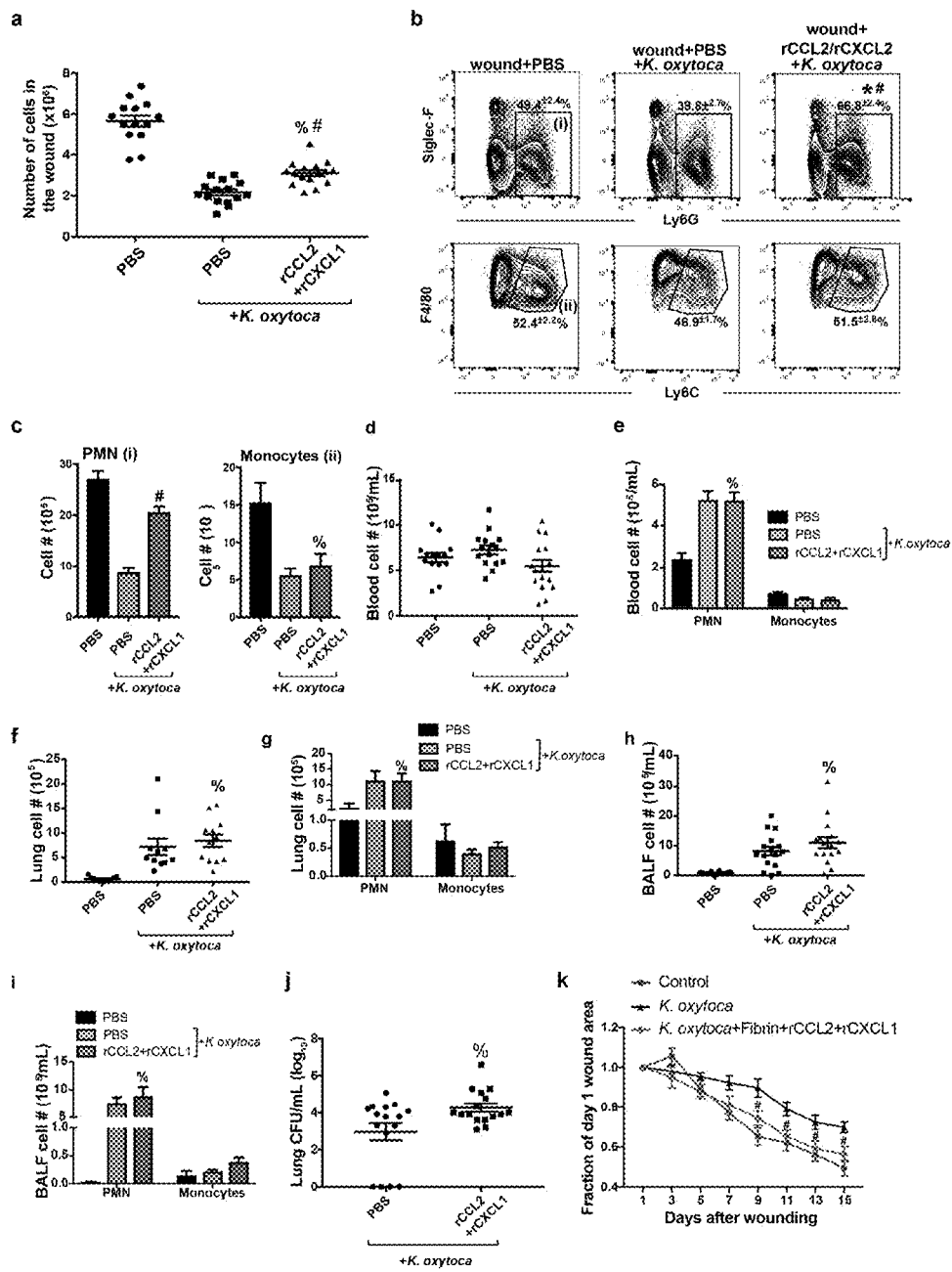
FIG. 5 shows that the addition of exogenous CCL2 and CXCL1 to wounds improves healing at the expense of pulmonary resistance to *K. oxytoca* infection. Mice with PVA sponge wounds were uninfected or infected with *K. oxytoca* as shown in FIG. 1c. Sponges were injected with PBS vehicle or recombinant CCL2+CXCL1 on wound days 5 and 6. Wound and blood cellularity was determined on wound day 7 (FIG. 5a). The effect of chemokine administration on the innate immune cellular makeup of PVA sponge wounds from uninfected and infected mice was determined by flow cytometry. Infected mice that received exogenous chemokines had significantly more wound neutrophils by proportion (FIG. 5b) and total number (FIG. 5c) than infected mice without chemokine treatment. The effect of chemokine treatments on total blood cellularity is shown in FIG. 5d. The number of circulating neutrophils and F4/80$^+$Ly6C$^{hi}$ inflammatory monocytes in response to chemokine treatments was also determined (FIG. 5e). The cellularity of the lung tissue (FIG. 5f), the number of lung neutrophils and monocytes (FIG. 5g), the cellularity of the BALF (FIG. 5h) and number of BALF neutrophils and monocytes (FIG. 5i) were determined in wounded and infected mice with or without wound chemokine treatments. The effect of wound chemokine treatments on lung bacterial burden was determined by CFU analysis (FIG. 5j). Excisional tail wounds were performed on C57BL/6J mice, which were then uninfected or infected with K. oxytoca. Wound beds were left untreated, or treated with fibrin sealant with or without recombinant CCL2+CXCL1 as described herein. The area of the tail wound was measured to determine the effect of fibrin and chemokine application on the rate of wound closure. The combination of chemokines and fibrin significantly increased wound closure beginning on day 9 post-wounding (FIG. 5k). Data are shown as the mean ±SEM with minimum n=12 mice per group from three independent experiments. Results are considered statistically significant when p≤0.05.

CCL2 and CXCL1 treatment increased the day 7 wound cellularity of wound+*K. oxytoca* mice, compared to wound+*K. oxytoca* mice treated with PBS (FIG. 5a). The frequency and number of neutrophils was significantly increased in wound+*K. oxytoca* mice with the addition of exogenous cytokines. The number of monocytes was not significantly influenced despite the addition of the monocyte chemoattractant CCL2 (FIG. 5b and FIG. 5c). Wound chemokine treatments did not affect the number of circulating cells, including neutrophils and monocytes (FIG. 5d and FIG. 5e). Wound chemokine treatments also did not have a significant effect on the overall cellularity or the number of neutrophils and monocytes isolated from the lung tissue or BALF of wound+*K. oxytoca* mice (FIG. 5f-FIG. 5i). Bacterial titers were elevated in the infected mice that received wound chemokine treatments (FIG. 5j), suggesting that the redirection of neutrophil trafficking towards the wound had a detrimental effect on pulmonary bacterial resistance.

To determine whether the addition of exogenous chemokines could improve wound healing, recombinant CCL2 and CXCL1 were applied to the tail wounds of *K. oxytoca*-infected mice using a topical fibrin sealant. Recombinant CCL2 and CXCL1 were incorporated into the fibrin sealant prior to application. Fibrinolysis by wound site proteases delivers the fibrin-incorporated chemokines to the wound bed. The wounds of uninfected mice were left untreated (control) or were treated with fibrin sealant. A subset of tail-wounded mice was infected with *K. oxytoca* on wound day 1. The wound beds of tail wound+*K. oxytoca* mice were untreated, treated with fibrin sealant, or treated with fibrin sealant containing recombinant CCL2 and recombinant CXCL1. Treatments were applied every day from wounding days 1 to 7, then every other day from days 9 to 15.

Figure 12:
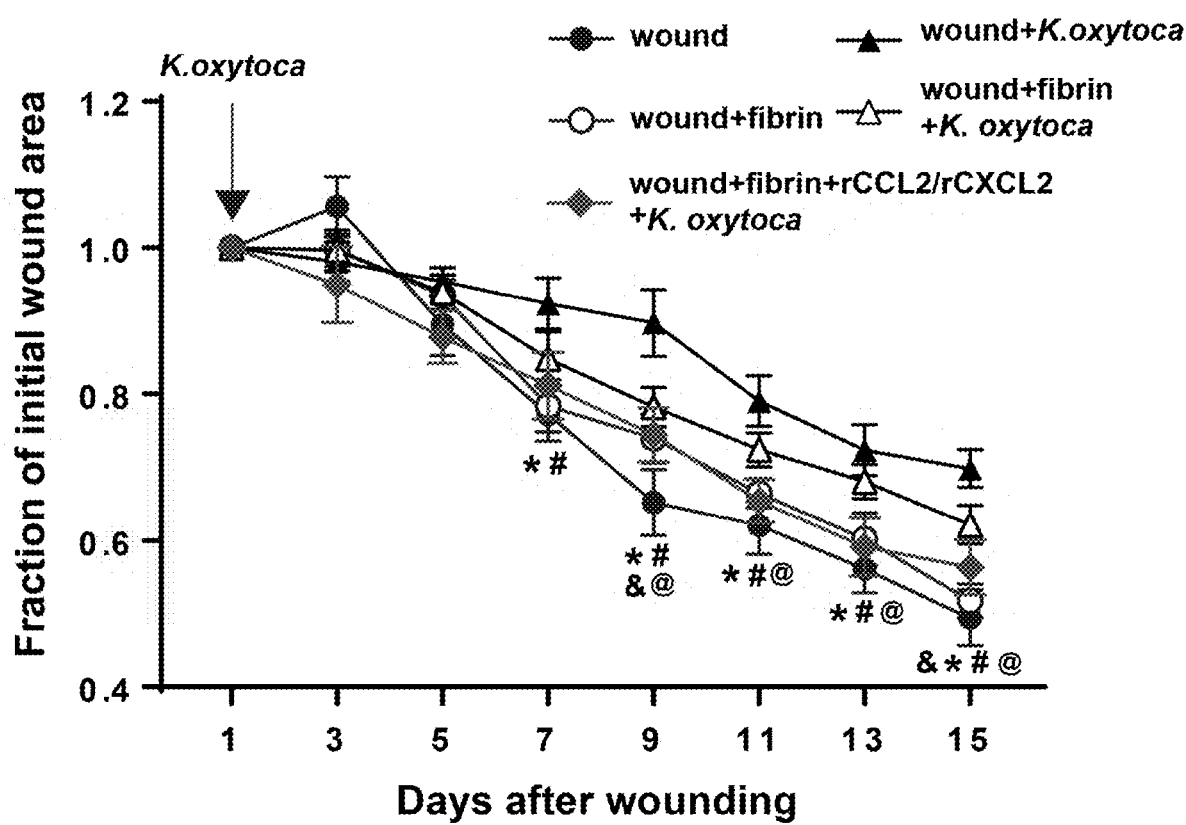
FIG. 12 shows the effect of fibrin sealant and exogenous recombinant chemokine treatment on excisional tail wound healing in mice with pulmonary K. oxytoca infection. Mice were wounded by tail skin excision. A cohort of wounded mice was infected intranasally with K. oxytoca one day later. Wounds remained untreated, were treated with a fibrin sealant (Tisseel), or were treated with a fibrin sealant supplemented with recombinant CCL2 and CXCL2 as described herein. The effects of the various treatments on the rate of tail wound closure are presented. Fibrin treatment alone did not significantly alter the rate of tail wound closure in infected mice, whereas the combination of fibrin sealant and recombinant CCL2/CXCL1 significantly accelerated wound closure beginning on would day 9. * indicates a statistically significant change between wound (uninfected) and wound+K. oxytoca, #indicates a statistically significant change between wound+fibrin and wound+K. oxytoca, & indicates a statistically significant change between wound and wound+fibrin+K. oxytoca, @ indicates a statistically significant change between wound+*K. oxytoca* and wound+fibrin+rCCL2/rCXCL1+*K. oxytoca* infection.

*K. oxytoca*-infected mice had the slowest healing tail skin wounds (FIG. 5k). Application of fibrin sealant to the tail skin wounds of control or *K. oxytoca*-infected mice did not significantly affect the rate of healing (FIG. 12). However, treatment of tail skin wounds with fibrin supplemented with recombinant CCL2 and recombinant CXCL1 restored the rate of healing in *K. oxytoca*-infected mice to that of the control group (FIG. 5k). Interestingly, application of fibrin sealant to the tail skin wounds with recombinant CCL2 alone or with recombinant CXCL1 alone in *K. oxytoca*-infected mice did not significantly affect the rate of healing (data not shown). Accordingly, the combination of recombinant CCL2 and recombinant CXCL1 may be important to restore the rate of healing in *K. oxytoca*-infected mice to that of the control group.

These data suggest that chemokine-mediated signals control the rate of tail skin wound closure, likely through the increased recruitment of innate leukocytes to the wound site.

Discussion

The studies described herein investigated the concept of innate immune prioritization of inflammatory sites, inspired by clinical data demonstrating that surgical patients experienced higher rates of abdominal incision dehiscence when diagnosed with pneumonia (Table 3). Innate leukocytes are critical to the repair of injured tissue and to the early control of pulmonary infection, so to investigate the role played by the innate immune system, we developed a murine model of post-injury pulmonary infection. In this model, the innate immune response is faced with two distal and competing inflammatory insults. There is considerable overlap in the cellular and cytokine responses that orchestrate acute wound healing and the pulmonary response to bacterial infection.[3-5,7-9,12,13,19,22,23,27,39,41-48] Therefore, we hypothesized that one inflammatory site would more strongly recruit innate leukocytes, and thus take priority over the other in a concept we call "immune triage." In this model, the pulmonary response to bacterial infection was prioritized at the expense of cutaneous wound healing. This effect was controlled in part by chemokine-directed innate leukocyte trafficking, which diverted monocytes and neutrophils away from the wound. When leukocyte trafficking to the wound was restored by the addition of exogenous chemokines there was a small, but significant, impact on the bacterial clearance in the lung, furthering the idea of an essential prioritization of the innate immune response when faced with multiple insults.

The data presented herein demonstrate that the healing rate of excisional tail wounds was delayed following the onset of pulmonary *K. oxytoca* infection. Using the PVA sponge wound model to investigate the cellular mechanisms of impaired healing, we determined that pulmonary infection resulted in greatly reduced wound cellularity as well as cytokine and chemokine concentrations. The loss of wound cellularity was attributed primarily to a decrease in neutrophils and inflammatory monocytes. These leukocytes migrate from the blood to the wound site, where they clear injured tissue debris, coordinate inflammatory responses, and, in the case of monocytes, differentiate into wound macrophages, which drive repair responses.[4,7,12] Using congenic bone marrow transfer experiments, we demonstrated that the onset of pulmonary bacterial infection abruptly disrupted the ability of monocytes and neutrophils to migrate to the wound site. Blocking the early acute cellular responses to wounding has been shown to disrupt the later stages of healing,[1,5,6,9,27] as demonstrated by the data we present here. It has been reported that injury or infection can induce systemic immunosuppression,[28,35,49,50] which we hypothesized could contribute to the impaired wound healing that occurred in mice with pulmonary bacterial infection. Evidence of this was seen in the delayed expression of TNF-α and CXCL1 in the plasma of wound+*K. oxytoca* mice compared to infected mice alone. TNF-α has coordinated expression with many chemokines, including CXCL1, suggesting that the deficit in these factors may be linked.[51-55] The decrease in systemic TNF-α and CXCL1 reflected a similar trend observed in the BALF, suggesting that the systemic effect was driven by a transient suppression of local cytokine and chemokine signaling in the lung. Surprisingly, the suppressive effect of wounding on BALF cytokine and chemokine levels during *K. oxytoca* infection did not have an overtly detrimental effect on BALF cellularity or the control of bacterial infection. Perhaps this is due to the lung being a highly vascularized space, thus permitting even low levels of chemokines to attract an adequate number of cells to respond to infection. This is likely why wound+*K. oxytoca* mice were able to mediate early control over *K. oxytoca* infection at the time points examined.

Despite the transient depression in systemic cytokine and chemokine signaling, wounding bolstered blood cellularity in both uninfected and infected mice. In particular, there were twice as many circulating neutrophils in wound+*K.*

*oxytoca* mice compared to other treatment groups. Despite the surplus of circulating neutrophils, the wounds of wound+ *K. oxytoca* mice had very few neutrophils compared to the wounds of uninfected mice. This indicates that a lack of neutrophil chemotactic signal from the wound site was responsible for the decreased number of wound neutrophils in wound+*K. oxytoca* mice. In contrast, the number of circulating Ly6C$^{hi}$ monocytes was lowest in wound+*K. oxytoca* mice, so the decrease in wound monocyte number in *K. oxytoca*-infected mice may reflect both a decrease in the circulating supply and a loss of chemotactic signal from the wound. Adoptive transfer experiments demonstrated decreased accumulation of naïve donor bone marrow neutrophils and monocytes in the wounds of wound+*K. oxytoca* recipient mice compared to wounded recipients alone. Infected mice had decreased wound fluid concentrations of monocyte and neutrophil chemoattractants including CCL2 and CXCL1. Together, these data suggest that the onset of infection suppressed local chemokine responses in the wound, which attenuated innate leukocyte migration to the injured site.

We hypothesized that redirecting neutrophil and monocyte trafficking to the wounds of wound+*K. oxytoca* mice would improve healing. Serial application of recombinant CCL2 and CXCL1 with a fibrin sealant to excisional tail skin wound beds accelerated wound closure in *K. oxytoca*-infected mice. Mice with this treatment had completely restored wound healing to the levels of uninfected mice. To determine how these chemokine treatments altered the cellularity of the wound, we used the PVA sponge model. Injection of recombinant CCL2 and CXCL1 into PVA sponge wounds partially restored wound cellularity in wound+*K. oxytoca* mice, primarily through an increase in neutrophils. Neutrophils were the predominant circulating leukocyte population in infected mice. This is likely why they were preferentially recruited to the wound compared to inflammatory monocytes in wound+*K. oxytoca* mice treated with recombinant chemokines. PVA sponge-wounded and infected mice that received wound chemokine treatments showed a slight impairment in bacterial clearance in the lungs. This suggested that the redistribution of neutrophils to the wound was enough to alter pulmonary resistance to bacterial infection. Surprisingly, there was not a decrease in overall cellularity in the lung or BALF, including neutrophils and monocytes. The reason for this loss of resistance to bacterial infection will require further investigation but was perhaps driven by impaired activation or bactericidal activity of the cells.

The studies presented herein provide insight into how the innate immune response is equipped to handle simultaneous distal inflammatory insults. Taken together, these data demonstrate that the innate immune response can prioritize its response to one inflammatory site, in this case an infected lung, over a second simultaneously occurring inflammatory event such as a cutaneous wound. Altering this balance through chemokine signaling shifted the immune response towards wound repair. Together, these studies demonstrate that distal inflammatory insults compete for innate immune cellular resources, and prioritization of the immune response towards one inflamed site over the other is dictated by chemokine-mediated signals.

REFERENCES

1. DiPietro, L. A., et al. (1998). MIP-1alpha as a critical macrophage chemoattractant in murine wound repair. Journal of Clinical Investigation 101, 1693-1698.
2. Daley, J. M., et al (2005). Modulation of macrophage phenotype by soluble product(s) released from neutrophils. J. Immunol. 174, 2265-2272.
3. Daley, J. M., et al (2010). The phenotype of murine wound macrophages. Journal of Leukocyte Biology 87, 59-67.
4. Lucas, T., et al. (2010). Differential Roles of Macrophages in Diverse Phases of Skin Repair. The Journal of Immunology 184, 3964-3977.
5. Mirza, R., et al. (2010). Selective and Specific Macrophage Ablation Is Detrimental to Wound Healing in Mice. The American Journal of Pathology 175, 2454-2462.
6. Low, Q. E. H. et al (2010). Short Communication. The American Journal of Pathology 159, 457-463
7. Brancato, S. K. and Albina, J. E. (2011). Wound Macrophages as Key Regulators of Repair. The American Journal of Pathology 178, 19-25.
8. Brancato, S. K., et al. (2013). Toll-like receptor 4 signaling regulates the acute local inflammatory response to injury and the fibrosis/neovascularization of sterile wounds. Wound Repair Regen 21, 624-633.
9. He, L. and Marneros, A. G. (2013). Macrophages Are Essential for the Early Wound Healing Response and the Formation of a Fibrovascular Scar. The American Journal of Pathology 182, 2407-2417.
10. Novak, M. L. and Koh, T. J. (2013). Phenotypic Transitions of Macrophages Orchestrate Tissue Repair. The American Journal of Pathology 183, 1352-1363.
11. Kim, M.-H., et al (2013). Catecholamine Stress Alters Neutrophil Trafficking and Impairs Wound Healing by. Journal of Investigative Dermatology 134, 809-817.
12. Crane, M. J., et al. (2014). The Monocyte to Macrophage Transition in the Murine Sterile Wound. PLoS ONE 9(1): e86660.
13. Mirza, R. E. and Koh, T. J. (2014). Contributions of cell subsets to cytokine production during normal and impaired wound healing. CYTOKINE 1-4.
14. Vaddi, K. and Newton, R. C. (1994). Regulation of monocyte integrin expression by beta-family chemokines. J. Immunol. 153, 4721-4732.
15. Eash, K. J., et al. (2010). CXCR2 and CXCR4 antagonistically regulate neutrophil trafficking from murine bone marrow. Journal of Clinical Investigation 120: 2423-2431.
16. Rzeniewicz, K., et al. (2015). L-selectin shedding is activated specifically within transmigrating pseudopods of monocytes to regulate cell polarity in vitro. Proceedings of the National Academy of Sciences 112(12): E1461-E1470.
17. Vincent, J. L., et al. (1995). The prevalence of nosocomial infection in intensive care units in Europe. Results of the European Prevalence of Infection in Intensi$^v$e Care (EPIC) Study. EPIC International Advisory Committee. JAMA 274, 639-644.
18. Vincent, J. L., (2003). Nosocomial infections in adult intensive-care units. The Lancet 361, 2068-2077
19. Manderscheid, P. A., et al (2004). Bacterial clearance and cytokine profiles in a murine model of postsurgical nosocomial pneumonia. Clin. Diagn. Lab. Immunol. 11, 742-751.
20. Daubin, C., et al. (2005). Nosocomial viral ventilator-associated pneumonia in the intensive care unit: a prospective cohort study. Intensive Care Medicine 31, 1116-1122.
21. Lee, K. M., et al (2018), Coinfection with Influenza A Virus and *Klebsiella oxytoca*: An Underrecognized Impact on Host Resistance and Tolerance to Pulmonary Infections. Front. Immunol. 9, 1041.

22. Olszewski, M. A., et al. (2007). Effect of Laparotomy on Clearance and Cytokine Induction in *Staphylococcus aureus*—infected Lungs. American Journal of Respiratory and Critical Care Medicine 176, 921-929.
23. Jonker, M. A., et al. (2011). Injury Induces Localized Airway Increases in Pro-Inflammatory Cytokines in Humans and Mice. Surgical Infections 12, 49-56.
24. Jonker, M. A., et al (2010). Proinflammatory Cytokine Surge After Injury Stimulates an Airway Immunoglobulin A Increase. The Journal of Trauma: Injury, Infection, and Critical Care 69, 843-848.
25. Feltes, C. M., et al (2011). Pulmonary Endothelial Cell Activation During Experimental Acute Kidney Injury. Shock 36, 170-176.
26. Crane, M. J., et al. (2018). Pulmonary influenza A virus infection leads to suppression of the innate immune response to dermal injury. PLoS Pathog 14, e1007212.
27. Duffield, J. S., et al. (2005). Selective depletion of macrophages reveals distinct, opposing roles during liver injury and repair. Journal of Clinical Investigation 115, 56-65.
28. Angele, M. K. and Faist, E. (2002). Clinical review: immunodepression in the surgical patient and increased susceptibility to infection. Critical care (London, England) 6, 298-305.
29. Huber-Lang, M., et aL (2018). Innate immune responses to trauma. Nature Immunology 19, 327-341.
30. Marshall, C. D., et al. (2018). Cutaneous Scarring: Basic Science, Current Treatments, and Future Directions. Advances in Wound Care 7, 29-45.
31. Lord, J. M., et al. (2014). The systemic immune response to trauma: an overview of pathophysiology and treatment. Lancet (London, England) 384, 1455-1465.
32. Gould, L., et al. (2015). Chronic Wound Repair and Healing in Older Adults: Current Status and Future Research. Journal of the American Geriatrics Society 63, 427-438.
33. Sen, C. K., et al (2009). Human skin wounds: A major and snowballing threat to public health and the economy. Wound Repair and Regeneration 17, 763-771.
34. Nussbaum, S. R., et al. (2018). An Economic Evaluation of the Impact, Cost, and Medicare Policy Implications of Chronic Nonhealing Wounds. Value in Health 21, 27-32.
35. Hensler, T., et al. (1997). Distinct mechanisms of immunosuppression as a consequence of major surgery. Infection and immunity 65, 2283-2291.
36. Falanga, V., et al. (2004). Full-thickness Wounding of the mouse tail as a model for delayed wound healing: accelerated wound closure in Smad3 knock-out mice. Wound Repair and Regeneration 12, 320-326.
37. Falanga, V., et al (2007). Autologous Bone Marrow-Derived Cultured Mesenchymal Stem Cells Delivered in a Fibrin Spray Accelerate Healing in Murine and Human Cutaneous Wounds. Tissue Engineering 13, 1299-1312,
38. Herzog, K. A. T., et al. (2014). Genotypes of *Klebsiella oxytoca* Isolates from Patients with Nosocomial Pneumonia Are Distinct from Those of Isolates from Patients with Antibiotic-Associated Hemorrhagic Colitis. Journal of Clinical Microbiology 52, 1607-1616.
39. Thomay, A. A., et al. (2009). Disruption of Interleukin-1 Signaling Improves the Quality of Wound Healing. The American Journal of Pathology 174, 2129-2136.
40. Crane, M. J., et al (2009). Regulation of inflammatory monocyte/macrophage recruitment from the bone marrow during murine cytomegalovirus infection: role for type I interferons in localized induction of CCR2 ligands. J. Immunol. 183, 2810-2817.
41. Craig, A., et al. (2009). Neutrophil Recruitment to the Lungs during Bacterial Pneumonia. Infection and immunity 77, 568-575.
42. Mei, J., et al. (2010). CXCL5 Regulates Chemokine Scavenging and Pulmonary Host Defense to Bacterial Infection. Immunity 33, 106-117.
43. Yamarnoto, K., et al. (2013). Roles of Lung Epithelium in Neutrophil Recruitment During Pneumococcal Pneumonia, American Journal of Respiratory Cell and Molecular Biology, 50(2): 253-262.
44. Bordon, J., et alt (2013). Understanding the roles of cytokines and neutrophil activity and neutrophil apoptosis in the protective versus deleterious inflammatory response in pneumonia. International Journal of Infectious Diseases 17, e76-e83.
45. Jamieson, A. M., et al. (2013). Role of Tissue Protection in Lethal Respiratory Viral-Bacterial Coinfection. Science 340, 1230-1234,
46. Quinton, L. J. and Mizgerd, J. P. Dynamics of Lung Defense in Pneumonia: Resistance, Resilience, and Remodeling. Annu. Rev. Physiol. 77, 407-430 (2015).
47. Rendon, A., et al. (2016). Relevant Cytokines in the Management of Community-Acquired Pneumonia. Curr Infect Dis Rep 18, 71.
48. Pechous, R. D. (2017), With Friends Like These: The Complex Role of Neutrophils in the Progression of Severe Pneumonia. Front. Cell. Infect. Microbiol. 7, 119.
49. Jamieson, A. M., et al (2010). Influenza Virus-Induced Glucocorticoids Compromise Innate Host Defense against a Secondary Bacterial Infection. Cell Host & Microbe 7, 103-114.
50. Ding, N., et al (2012). Role of p38 mitogen-activated protein kinase in posttraumatic immunosuppression in mice. Journal of Trauma and Acute Care Surgery 73, 861-868.
51. Vieira, SM., et at (2009). A crucial role for TNF-$\alpha$ in mediating neutrophil influx induced by endogenously generated or exogenous chemokines, KC/CXCL1 and LIX/CXCL5. British Journal of Pharmacology 158, 779-789.
52. Yao, L., et al. (2013). Elevated CXCL1 expression in gp130-deficient endothelial cells impairs neutrophil migration in mice. Blood 122, 3832-3842.
53. Finsterbusch, M., et al. (2014). Neutrophils recruited by chemoattractants in vivo induce microvascular plasma protein leakage through secretion of TNF. The Journal of experimental medicine 211, 1307-1314.
54. Shieh, J. M., et al. (2014). CXCL1 Regulation in Human Pulmonary Epithelial Cells by Tumor Necrosis Factor. Cell Physiol. Biochem. 34, 1373-1384.
55. Lo, H.-M. et al. (2014). TNF-$\alpha$ induces CXCL1 chemokine expression and release in human vascular endothelial cells in vitro via two distinct signaling pathways. Acta Pharmacologica Sinica 35, 339 EP.
56. See, e.g., Isselbacher et al. (1996). Harrison's Principles of Internal Medicine 13 ed., 1814-1882.
57. Iida N, Grotendorst G R (1990). Cloning and sequencing of a new gro transcript from activated human monocytes: expression in leukocytes and wound tissue. Mol. Cell. Biol. 10 (10): 5596-5599.
58. Becker S, et al. (1994). Constitutive and stimulated MCP-1, GRO alpha, beta, and gamma expression in human airway epithelium and bronchoalveolar macrophages. Am. J. Physiol. 266 (3 Pt 1): L278-L286.
59. Moser B, et al. (1990). Neutrophil-activating properties of the melanoma growth-stimulatory activity. J. Exp. Med. 171 (5): 1797-1802.

60. Schumacher C, et al. (1992). High- and low-affinity binding of GRO alpha and neutrophil-activating peptide 2 to interleukin 8 receptors on human neutrophils. Proc. Natl. Acad. Sci. U.S.A. 89 (21): 10542-10546.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize, or be able to ascertain using no more than routine experimentation, many equivalents to the specific embodiments described herein. Such equivalents are intended to be encompassed by the following claims.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

We claim:

1. A method for accelerating cutaneous wound healing in a subject afflicted with a pulmonary infection and/or a pulmonary injury, the method comprising the step of administering to the wound a composition comprising (a) one or more chemokine and (b) a fibrin carrier.

2. The method of claim 1, wherein the one or more chemokine is one or more inflammatory chemokine.

3. The method of claim 2, wherein the one or more inflammatory chemokine is a combination of one or more monocyte chemoattractant and one or more neutrophil chemoattractant.

4. The method of claim 3, wherein the one or more monocyte chemoattractant is selected from the group consisting of: CXCL4, CXCL10, CXCL17, CX3CL1, CCL1, CCL2, CCL3, CCL4, CCL5, CCL6, CCL7, CCL8, CCL12, CCL13, CCL14, CCL15, CCL16, CCL22, and CCL23.

5. The method of claim 3, wherein the one or more neutrophil chemoattractant is selected from the group consisting of: CXCL1, CXCL2, CXCL3, CXCL4, CXCL5, CXCL6, CXCL7, CXCL8, CXCL15, CCL9, CCL10, CCL20, CCL23, and CCL24.

6. A method for accelerating cutaneous wound healing in a subject afflicted with a pulmonary infection and/or a pulmonary injury, the method comprising the step of administering to the wound a composition comprising (a) one or more monocyte chemoattractant; (b) one or more neutrophil chemoattractant; and (c) a fibrin carrier.

7. The method of claim 6, wherein the one or more monocyte chemoattractant is selected from the group consisting of: CXCL4, CXCL10, CXCL17, CX3CL1, CCL1, CCL2, CCL3, CCL4, CCL5, CCL6, CCL7, CCL8, CCL12, CCL13, CCL14, CCL15, CCL16, CCL22, and CCL23.

8. The method of claim 6, wherein the one or more neutrophil chemoattractant is selected from the group consisting of: CXCL1, CXCL2, CXCL3, CXCL4, CXCL5, CXCL6, CXCL7, CXCL8, CXCL15, CCL9, CCL10, CCL20, CCL23, and CCL24.

9. A method for accelerating cutaneous wound healing in a subject afflicted with a pulmonary infection and/or a pulmonary injury, the method comprising the step of administering to the wound a composition comprising (a) CCL2, (b) CXCL1, and (c) a fibrin carrier.

10. The method according to claim 1, wherein the step is executed about one time per day for a time period of about 7 days and then about every other day after the about 7 days, or until the wound has healed.

11. The method according to claim 6, wherein the step is executed about one time per day for a time period of about 7 days and then about every other day after the about 7 days, or until the wound has healed.

12. The method according to claim 9, wherein the step is executed about one time per day for a time period of about 7 days and then about every other day after the about 7 days, or until the wound has healed.

* * * * *